United States Patent
Cope et al.

(10) Patent No.: US 12,005,122 B2
(45) Date of Patent: *Jun. 11, 2024

(54) COMPOUNDS AND METHODS FOR DIAGNOSIS AND TREATMENT OF VIRAL INFECTIONS

(71) Applicant: Navidea Biopharmaceuticals, Inc., Columbus, OH (US)

(72) Inventors: Frederick O. Cope, Westerville, OH (US); David A. Ralph, Columbus, OH (US)

(73) Assignee: Navidea Biopharmaceuticals, Inc., Columbus, OH (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/323,223

(22) Filed: May 18, 2021

(65) Prior Publication Data

US 2021/0338827 A1 Nov. 4, 2021

Related U.S. Application Data

(63) Continuation of application No. 15/729,635, filed on Oct. 10, 2017, now Pat. No. 11,007,272.

(60) Provisional application No. 62/405,780, filed on Oct. 7, 2016.

(51) Int. Cl.

| | |
|---|---|
| *A61K 47/61* | (2017.01) |
| *A61K 31/122* | (2006.01) |
| *A61K 31/351* | (2006.01) |
| *A61K 31/573* | (2006.01) |
| *A61K 39/395* | (2006.01) |
| *A61K 47/36* | (2006.01) |
| *A61K 47/68* | (2017.01) |
| *A61P 31/14* | (2006.01) |
| *C07K 16/28* | (2006.01) |
| *C08B 37/02* | (2006.01) |

(52) U.S. Cl.
CPC ............ *A61K 47/61* (2017.08); *A61K 31/122* (2013.01); *A61K 31/351* (2013.01); *A61K 31/573* (2013.01); *A61K 39/39566* (2013.01); *A61K 47/36* (2013.01); *A61K 47/6833* (2017.08); *A61K 47/6841* (2017.08); *A61P 31/14* (2018.01); *C07K 16/2896* (2013.01); *C08B 37/0021* (2013.01); *C12N 2770/24063* (2013.01)

(58) Field of Classification Search
CPC .... A61K 31/351; A61K 31/573; A61K 47/61; C08B 37/0021; A61P 31/14; C07K 14/70596; C07K 16/2896

See application file for complete search history.

(56) References Cited

U.S. PATENT DOCUMENTS

| | | | |
|---|---|---|---|
| 6,036,963 | A | 3/2000 | Weinkauf Ronni et al. |
| 6,409,990 | B1 | 6/2002 | Vera |
| 7,666,979 | B2 | 2/2010 | Fan et al. |
| 10,792,582 | B2 | 10/2020 | Qin et al. |
| 11,007,272 | B1 * | 5/2021 | Cope ................ A61K 47/6833 |
| 2004/0116348 | A1 | 6/2004 | Chau et al. |
| 2004/0122382 | A1 | 6/2004 | Johnson et al. |
| 2004/0241158 | A1 | 12/2004 | McBride et al. |
| 2005/0042248 | A1 | 2/2005 | Ahmad et al. |
| 2005/0214859 | A1 | 9/2005 | Dransfield et al. |
| 2009/0004218 | A1 | 1/2009 | Hacohen et al. |
| 2009/0311182 | A1 | 12/2009 | Wang et al. |
| 2010/0261875 | A1 | 10/2010 | Dransfield et al. |
| 2013/0330274 | A1 | 12/2013 | Berr et al. |
| 2014/0127301 | A1 | 5/2014 | Alexis et al. |
| 2014/0235790 | A1 | 8/2014 | Stayton et al. |
| 2015/0023876 | A1 | 1/2015 | Cope et al. |
| 2016/0206763 | A1 | 7/2016 | Cope |

FOREIGN PATENT DOCUMENTS

| | | |
|---|---|---|
| CA | 2974634 A1 | 7/2016 |
| CN | 1711091 A | 12/2005 |
| CN | 104684546 A | 6/2015 |
| CN | 105764529 A | 7/2016 |
| GB | 1069820 A | 5/1967 |
| JP | 2012516328 A | 7/2012 |
| WO | 9608263 A1 | 3/1996 |
| WO | 0069473 A3 | 11/2000 |
| WO | 2012169973 A1 | 12/2012 |
| WO | 2015013341 A1 | 1/2015 |
| WO | 2016011415 A2 | 1/2016 |
| WO | 2016011419 A1 | 1/2016 |
| WO | 2016011415 A3 | 3/2016 |

OTHER PUBLICATIONS

Calvet, "First detection of autochthonous Zika virus transmission in aHIV-infected patient in Rio de Janeiro, Brazil", Journal of Clinical Virology, 74, 2016, pp. 1-3.

Azad, "Exploitation of the Macrophage Mannose Receptor (CD206) in Infectious Disease Diagnostics and Therapeutics", Journal of Cytology & Molecular Biology, Jan. 2014, Issue 1, vol. 1.

Hamel, "Biology of Zika Virus Infection in Human Skin Cells", Journal of Viralogy, Sep. 2015, vol. 89, No. 17, pp. 8880-8896.

Kratz, "Drug-Polymer Conjugates Containing Acid-Cleavable Bonds", Critical Reviews in Therapeutic Drug Carrier Systems, 1999, 0743-4863/99.

Schmaljohann, "Thermo- and pH-responsive polymers in drug delivery", Science Direct, Adavanced Drug Delivery Reviews, 2006, 1655-1670.

(Continued)

*Primary Examiner* — Theodore R. Howell

(74) *Attorney, Agent, or Firm* — Fredrikson & Byron, P.A.

(57) ABSTRACT

Compositions and methods of using these compositions that can include a targeting moiety and a therapeutic agent are described herein. These compositions can be used for diagnosing and/or treating flaviviridae—family viruses including Zika virus, dengue virus, and yellow fever.

20 Claims, 7 Drawing Sheets

(56) References Cited

OTHER PUBLICATIONS

Fakhriedzwan Idris et al., "Glycosylation of Dengue Virus Glycoproteins and Their Interactions With Carbohydrate Receptors: Possible Targets for Antiviral Therapy", "Archives of Virology", Apr. 11, 2016, pp. 1751-1760, vol. 161, No. 7.
Lammers, W., "Some Pharmacological Effects of Trithylamine", "Acta Physiol Pharmacol Neerlandica", Jan. 1, 1959, pp. 31-39, vol. 8, No. 1.
Takiura et al., "Studies of Oligosaccharides X. Synthesis of Isomaltose and Isomaltotriose by Benzyl Blocking Method", "Chem Pharm Bull, J. Org. Chem", Jan. 1, 1972, p. 527.
Miller, "The Mannose Receptor Mediates Dengue Virus Infection of Macrophages", PLOS Pathogens, Feb. 2008, vol. 4, Issue 2, 0001-0011.
Arboleda Alzate, "Humanmacrophages differentiated in the presence of vitamin D3 restrict dengue virus infection and innate responses by downregulatingmannose receptor expression", 2017, PLOS Neglected Tropical Diseases, 1-18.
Schaeffer, "Dermal CD14+ Dendritic Cell and MacrophageInfection by Dengue Virus Is Stimulated by Interleukin-4", Journal of Investigative Dermatology, 2015, 1743-1751.
Anonymous, C:\EPODATA\SEA\eplogf\ep17207291.log, Sep. 29, 2008.
Idris et al. "Glycosylation of dengue virus glycoproteins and their interactions with carbohydrate receptors: Possible targest for antiviral therapy", Arch. Virol., 2016, 161, 1751-1760.
Allavena, P., et al., "Engagement of the man nose receptor by tumoral mucins activates an immune suppressive phenotype in human tumor-associated macrophages," Clin. Dev. Immunol. 2010: 547179.
Balkwill, F., et al., "Inflammation and cancer: back to Virchow?" Lancet 357: 2001, pp. 539-545.
Banerji, S., et al., "LYVE-1, a new homologue of the CD44 glycoprotein, is a lymph-specific receptor for Hyaluronan," J Cell Biol. 144: 1999, pp. 789-801.
Beasley, N. J., et al., "Intratumoral lymphangiogenesis and lymph node metastasis in head and neck cancer," Cancer Res. 62: 2002, pp. 1315-1320.
Choe et al., "Targeted In Vivo Imaging of Angiogenesis: Present Status and Perspectives," 2007, Current Pharmaceutical Design, 13:17-31.
Choi, Y. K., et al., "Characterization of cells expressing lymphatic marker LYVE-1 in macaque large intestine during simian immunodeficiency virus infection identifies a large population of non-vascular LYVE-1(+)/DC-SIGN(+) cells," Lymphat. Res. Biol. 11: 2013, pp. 26-34.
Coessens et al., "Synthesis of polyglutamine and dextran conjugates of streptomycin with an acid-sensitive drug-carrier linkage," Journal of Controlled Release, 1996, vol. 38, No. 2, pp. 141-150.
Coughlin, A., et al., "Oral cavity squamous cell carcinoma and the clinically n0 neck: the past, present, and future of sentinel lymph node biopsy," Curr. Oncol. Rep. 12: 2010, pp. 129-135.
Dave, S.S., et al., "Molecular diagnosis of Burkitt's lymphoma," N. Engl. J. Med. 354: 2006, pp. 2431-2442.
Dijkgraaf et al., "Molecular imaging of angiogenesis with SPECT," 2010, Eur. J. Nucl. Med. Mol. Imaging, published online Sep. 21, 2010.
Ellner, S. J., et al., "Dose-dependent biodistribution of [(99m)Tc]DTPA-mannosyl-dextran for breast cancer sentinel lymph node mapping," Nucl. Med. Biol. 30: 2003, pp. 805-810.
Ellner, S. J., et al., "Sentinel lymph node mapping of the colon and stomach using lymphoseek in a pig model," Ann. Surg. Oncol. 11: 2004, pp. 674-681.
Engering, A., et al., "The dendritic cell-specific adhesion receptor DC-SIGN internalizes antigen for presentation to T cells," J. Immunol. 168: 2002, pp. 2118-2126.
Emerson et al., "A Receptor-targeted Fluorescent Radiopharmaceutical for Multireporter Sentinel Lymph Node Imaging," Radiology, 2012, 265(1):186-193.

Farinha, P., et al., "The architectural pattern of FOXP3-positive T cells in follicular lymphoma is an independent predictor of survival and histologic transformation," Blood, 115: 2010, pp. 289-295.
Gazi, U., et al., "Influence of the mannose receptor in host immune responses," Immunobiology 214: 2009, pp. 554-561.
Geijtenbeek, T. B., et al., "Self- and nonself-recognition by C-type lectins on dendritic cells," Annu. Rev. Immunol. 22: 2004, pp. 33-54.
Gordon, S., "Pattern recognition receptors: doubling up for the innate immune response," Cell 111: 2002, pp. 927-930.
Gordon, S., "Alternative activation of macrophages," Nat. Rev. Immunol. 3: 2003, pp. 23-35.
Hattori, Y., et al., "Enhanced DNA vaccine potency by mannosylated lipoplex after intraperitoneal administration," J Gene Med 8: 2006, pp. 824-834.
Henning, L. N., et al., "Pulmonary surfactant protein A regulates TLR expression and activity in human macrophages," J. Immunol. 180: 2008, pp. 7847-7858.
Hoh, C. K., et al., "Preclinical studies of [(99m)Tc]DTPA-mannosyl-Dextran," Nucl. Med. Biol. 30: 2003, pp. 457-464.
Hongjing et al., "Facile preparation and drug delivery behaviour of novel dextran-based nanogels conjugated with doxorubicin via a pH-labile bond," Journal of Controlled Release, 2013, vol. 172, No. 1, pp. e67-e68.
Irjala, H., et al., "Mannose receptor is a novel ligand for L-selectin and mediates lymphocyte binding to lymphatic endothelium," J. Exp. Med. 194: 2001, pp. 1033-1042.
Irjala, H., et al., "Mannose receptor (MR) and common lymphatic endothelial and vascular endothelial receptor (CLEVER)-1 direct the binding of cancer cells to the lymph vessel endothelium," Cancer Res. 63: 2003, pp. 4671-4676.
Jarjour et al., "Fluorescent CD206-targeted Manocept-Cy3 (Mano-Cy3) specifically localizes on macrophages (MPs) derived from rheumatoid arthritis (RA) patients' synovial fluid & is quantitatively greater than that from non-RA patients," J Nucl Med, 2014, 55(1):1229.
Jensen, T. O., et al., "Macrophage markers in serum and tumor have prognostic impact in American Joint Committee on Cancer stage I/II melanoma," J. Clin. Oncol. 27: 2009, pp. 3330-3337.
Kamper, P., et al., "Tumor-infiltrating macrophages correlate with adverse prognosis and Epstein-Barr virus status in classical Hodgkin's lymphoma," Haematologica 96: 2011, pp. 269-276.
Kang, B. K., et al., "The human macrophage mannose receptor directs *Mycobacterium tuberculosis* lipoarabinomannan-mediated phagosome biogenesis," J Exp. Med 202: 2005, pp. 987-999.
Kawakami, S., et al., "Mannose receptor-mediated gene transfer into macrophages using novel mannosylated cationic liposomes," Gene Ther. 7: 2000, pp. 292-299.
Kurahara, H., et al., "Significance of M2-polarized tumor-associated macrophage in pancreatic cancer," J. Surg. Res. 167: 2011, pp. e211-e219.
Lau, S. K., et al., "CD163: a specific marker of macrophages in paraffin-embedded tissue samples," Am. J. Clin. Pathol. 122: 2004, pp. 794-801.
Law, S. K. A., et al., "A new macrophage differentiation antigen which is a member of the scavenger receptor superfamily," Eur. J. Immunol. 23: 1993, pp. 2320-2325.
Lee, C. H., et al., "Prognostic significance of macrophage infiltration in leiomyosarcomas," Clin. Cancer Res. 14: 2008, pp. 1423-1430.
Lee, S. J., et al., "Mannose receptor-mediated regulation of serum glycoprotein Homeostasis," Science 295: 2002, p. 1901.
Leek, R. D., et al., "Association of macrophage infiltration with angiogenesis and prognosis in invasive breast carcinoma," Cancer Res. 56: 1996, pp. 4625-4629.
Leong, S. P., et al., "A phase 2 study of (99m)Tc-tilmanocept in the detection of sentinel lymph nodes in melanoma and breast cancer," Ann. Surg. Oncol. 18: 2011, pp. 961-969.
Leon-Rodriguez et al., "The Synthesis and Chelation Chemistry of DOTA-Peptide Conjugates," Bioconjugate Chemistry, Jan. 3, 2008, 19(2):391-402.
Li et al., "Cu-Labeled Tetrameric and Octameric RGD Peptides for Small-Animal PET of Tumor avb3 Integrin Expression," 2007, J. Nuclear Medicine, 48:1162-1171.

(56) References Cited

OTHER PUBLICATIONS

Li et al., "Synthesis and characterization of a high-affinity αvβ6-specific ligand for in vitro and in vivo applications," 2009, Mol. Cancer Ther., 8:5:1239-1249.

Locke, L. W., et al., "PET imaging of tumor associated macrophages using mannose coated 64Cu liposomes," Biomaterials 33: 2012, pp. 7785-7793.

Lu, Y., et al., "Development of an antigen-presenting cell-targeted DNA vaccine against melanoma by mannosylated liposomes," Biomaterials 28: 2007, pp. 3255-3262.

Luo, Y., et al., "Targeting tumor-associated macrophages as a novel strategy against breast cancer," J. Clin. Invest 116: 2006, pp. 2132-2141.

Mantovani, A., et al., "The origin and function of tumor-associated macrophages," Immunol. Today 13: 1992, pp. 265-270.

Mantovani, A., et al., "Macrophage polarization: tumor-associated macrophages as a paradigm for polarized M2 mononuclear phagocytes," Trends Immunol. 23: 2002, pp. 549-555.

Marttila-Ichihara, F., et al., "Macrophage mannose receptor on lymphatics controls cell trafficking," Blood 112: 2008, pp. 64-72.

Mattila, M. M., et al., "VEGF-C induced lymphangiogenesis is associated with lymph node metastasis in orthotopic MCF-7 tumors," Int. J Cancer 98: 2002, pp. 946-951.

Maula, S. M., et al., "Intratumoral lymphatics are essential for the metastatic spread and prognosis in squamous cell carcinomas of the head and neck region," Cancer Res. 63: 2003, pp. 1920-1926.

McGrath et al., "CD206-targeted Cy3-Manocept (Mano-Cy3) localizes in nearly all cells present in Kaposi's sarcoma representing an opportunity for dynamic imaging, local staging and a potential for visceral metastasis imaging", Journal of Nuclear Medicine, 2014, 55(1):1681.

Mendez, J., et al., "Detection of gastric and colonic sentinel nodes through endoscopic administration of 99mTc-DTPA-mannosyl-dextran in pigs," J. Nucl. Med. 44: 2003, pp. 1677-1681.

Mills, C. D., et al., "M-1/M-2 macrophages and the Th1/Th2 paradigm," J. Immunol. 164: 2000, pp. 6166-6173.

Movahedi, K., et al., "Nanobodybased targeting of the macrophage mannose receptor for effective in vivo imaging of tumorassociated macrophages," Cancer Res. 72: 2012, pp. 4165-4177.

Nahrendorf et al., "F-4V for PET-CT imaging of VCAM-1 expression in inflammatory atherosclerosis," 2009, JACC Cardiovasc. Imaging, 2:10:1213-1222.

Park, S. M., et al., "Mapping the distinctive populations of lymphatic endothelial cells in different zones of human lymph nodes," PLoS. ONE. 9: 2014, e94781.

Paul C.B., Tertiary Pharmacology Review, Center For Drug Evaluation and Research, Aug. 10, 2011, 134 pages.

Petrova, T. V., et al., "Lymphatic endothelial reprogramming of vascular endothelial cells by the Prox-1 homeobox transcription factor," EMBO J 21: 2002, pp. 4593-4599.

Podgrabinska, S., et al., "Molecular characterization of lymphatic endothelial cells," Proc. Natl. Acad. Sci. U.S. A 99: 2002, pp. 16069-16074.

Porcheray F., et al., "Macrophage Activation and Human Immunodeficiency Virus Infection: HIV Replication Directs Macrophages towards a Pro-Inflammatory Phenotype While Previous Activation Modulates Macrophage Susceptibility to Infection and Viral Production," Virology, 2006, vol. 349 (1), pp. 112-120.

Puig-Kroger, A., et al., "Regulated expression of the pathogen receptor dendritic cell-specific intercellular adhesion molecule 3 (ICAM-3)-grabbing nonintegrin in THP-1 human leukemic cells, monocytes, and macrophages," J Biol Chem 279: 2004, pp. 25680-25688.

Rajaram, M. V., et al., "*Mycobacterium tuberculosis* lipomannan blocks TNF biosynthesis by regulating macrophage MAPK-activated protein kinase 2 (MK2) and microRNA miR-125b," Proc. Natl. Acad. Sci. U.S. A 108: 2011, pp. 17408-17413.

Rajaram, M. V., et al., "*Mycobacterium tuberculosis* activates human macrophage peroxisome proliferator-activated receptor gamma linking mannose receptor recognition to regulation of immune responses," J Immunol. 185: 2010, pp. 929-942.

Roseeuw et al., "Synthesis, Degradation, and Antimicrobial Properties of Targeted Macromolecular Prodrugs of Norfloxacin," Antimicrobial Agents and Chemotherapy, 2003, vol. 47, No. 11, pp. 3435-3441.

Rosol et al., "Intravenous administration (IV) of the CD206-targeted Manocept-Cy3 (Mano-Cy3) to mice with induced rheumatoid arthritis (RA) results in heterogeneous localization of Mano-Cy3 with strong specificity for RA-expressing joints," J Nucl Med, 2014, 55(1):1232.

Salem, C. E., et al., "A preclinical study of prostate sentinel lymph node mapping with [99mTC]diethylenetetramine pentaacetic acid-mannosyl-dextran," J. Urol. 175: 2006, pp. 744-748.

Salmi, M., et al., "CD44 binds to macrophage mannose receptor on lymphatic endothelium and supports lymphocyte migration via afferent lymphatics," Circ. Res. 112: 2013, pp. 1577-1582.

Schlesinger, L. S., "Macrophage phagocytosis of virulent but not attenuated strains of *Mycobacterium tuberculosis* is mediated by mannose receptors in addition to complement receptors," J. Immunol. 150: 1993, pp. 2920-2930.

Shabo, I., et al., "Expression of macrophage antigens by tumor cells," Adv. Exp. Med. Biol. 714: 2011, pp. 141-150.

Shabo, I., et al., "Breast cancer expression of CD163, a macrophage scavenger receptor, is related to early distant recurrence and reduced patient survival," Int. J. Cancer 123: 2008, pp. 780-786.

Shi, S. R., et al., "Antigen retrieval in formalin-fixed, paraffin-embedded tissues: an enhancement method for immunohistochemical staining based on microwave oven heating of tissue sections," J. Histochem. Cytochem. 39: 1991, pp. 741-748.

Skobe, M., et al., "Induction of tumor lymphangiogenesis by VEGF-C promotes breast cancer metastasis," Nat. Med 7: 2001, pp. 192-198.

Sosabowski et al., "Conjugation of DOTA-like chelating agents to peptides and radiolabeling with trivalent metallic isotopes," Nature Protocols 1, 2006, pp. 972-976.

Stahl, P., et al., "Receptormediated pinocytosis of mannose glycoconjugates by macrophages: characterization and evidence for receptor recycling," Cell 19: 1980, pp. 207-215.

Tahara, N., et al., "2-deoxy-2-[18F]fluoro-D-mannose positron emission tomography imaging in atherosclerosis," Nat. Med. 20: 2014, pp. 215-219.

Taylor, P. R., et al., "Macrophage receptors and immune recognition," Annu. Rev. Immunol. 23: 2005, pp. 901-944.

Taylor, P. R., et al., "The mannose receptor: linking homeostasis and immunity through sugar recognition," Trends Immunol. 26: 2005, pp. 104-110.

Torrelles, J. B., et al., "Role of C-type lectins in mycobacterial infections," Curr. Drug Targets. 9: 2008, pp. 102-112 (Abstract provided).

Trubian et al., New Drug Approvals 2013—Pt. XII-Technetium Tc 99m Tilmanocept (LymphoSeek) [online]. The ChEMBL-og. Aug. 30, 2013 [retrieved on Nov. 30, 2015]. Retrieved from the Internet: <URL: http://chembl.blogspot.com/2013/08/new-drug-approvals-2013-ptxii.html>, 4 pages.

Uccini et al., "Kaposi's Sarcoma Cells Express the Macrophage-Associated Antigen Mannose Receptor and Develop in Peripheral Blood Cultures of Kaposi's Sarcoma Patients," AJP Merch 1997, 150: 929-938.

Vera, D. R., et al., "[(99m)Tc]MAG(3)-mannosyl-dextran: a receptor-binding radiopharmaceutical for sentinel node detection," Nucl. Med. Biol. 28: 2001, pp. 493-498.

Vera, D. R., et al., "A synthetic macromolecule for sentinel node detection: (99m)Tc-DTPA-mannosyl-dextran," J. Nucl. Med. 42: 2001, pp. 951-959.

Vera, D. R., et al., "Kinetic sensitivity of a receptor-binding radiopharmaceutical: technetium-99m galactosyl-neoglycoalbumin," J. Nucl. Med. 30: 1989, pp. 1519-1530.

Vera, D. R., et al., "Tc-99m galactosyl-neoglycoalbumin: in vitro characterization of receptor-mediated binding," J. Nucl. Med. 25: 1984, pp. 779-787.

(56) References Cited

OTHER PUBLICATIONS

Vera, D.R. et al., "Cy5.5-DTPA-galactosyl-dextran: a fluorescent probe for in vivo measurement of receptor biochemistry," Nuclear Medicine and Biology, 32 (2005) pp. 687-693.

Wallace, A. M., et al., "Lymphoseek: a molecular radiopharmaceutical for sentinel node detection," Ann. Surg. Oncol. 10: 2003, pp. 531-538.

Wallace, A. M., et al., "Sentinel lymph node accumulation of Lymphoseek and Tc-99m-sulfur colloid using a '2-day' Protocol," Nucl. Med. Biol. 36: 2009, pp. 687-692.

Wallace, A. M., et al., Lymphoseek: a molecular imaging agent for melanoma sentinel lymph node mapping. Ann. Surg. Oncol. 14: 2007, pp. 913-921.

Wallace, A. M., et al., "Minimally invasive sentinel lymph node mapping of the pig colon with Lymphoseek," Surgery 139: 2006, pp. 217-223.

Wang et al., "A novel delivery system of doxorubicin with high load and pH-responsive release from the nano particles of poly (alpha, beta-aspartic acid) derivative," European Journal of Pharmaceutical Sciences, 2012, vol. 47, pp. 256-264.

Wild, J., et al., "Isolation of mannose-binding proteins from human and rat liver," Biochem. J. 210: 1983, pp. 167-174.

Wileman, T., et al., "Monensin inhibits recycling of macrophage mannose-glycoprotein receptors and ligand delivery to lysosomes," Biochem. J. 220: 1984, pp. 665-675.

Wilting, J., et al., "The transcription factor Prox1 is a marker for lymphatic endothelial cells in normal and diseased human tissues," FASEB J 16: 2002, pp. 1271-1273.

Yim et al., "Synthesis of DOTA-Conjugated Multimeric [Tyr3] Octreotide Peptides via a Combination of Cu(I)-Catalyzed "Click" Cycloaddition and Thio Acid/Sulfonyl Azide "Sulfo-Click" Amidation and Their in Vivo Evaluation," 2010, J. Med. Chem., 53:3944-3953.

Yu, S.S., et al., "Macrophage-Specific RNA Interference Targeting via "Click", Mannosylated Polymeric Micelles," Mol. Pharm., 2013.

\* cited by examiner

VERO Cells - Infectivity

| 100 | 51 | 89 | 83 | 87 | 93 | 104 | 53 | 73 |

PBS, Man-Dox 5μM, Man-Dox 1μM, Man17 5μM, Man17 1μM, Dex 5μM, Dex 1μM, Man-Dex 5μM, Man-Dex 1μM

Values for Agent as % of PBS (PBS Infectivity = 66 Plaques±4 S.D. in VERO Cells)

FIG. 5

COMPOUNDS AND METHODS FOR DIAGNOSIS AND TREATMENT OF VIRAL INFECTIONS

CROSS-REFERENCE TO RELATED APPLICATIONS

This application is a continuation application of U.S. application Ser. No. 15/729,635, filed Oct. 10, 2017, now U.S. Pat. No. 11,007,272, issued May 18, 2021, which claims priority to of U.S. Provisional Application No. 62/405,780 filed Oct. 7, 2016, the benefit of each of which is claimed hereby, and each of which are incorporated herein in its entirety.

DETAILED DESCRIPTION

Among other things, embodiments of the present invention are directed to compounds and compositions for targeting dermal macrophages. The present invention also provides methods of making such compounds and compositions. The present invention also provides diagnostic methods and methods of treatment using compounds comprising a dextran-based moiety, for uses including treating viral infections as disclosed herein.

The invention is not limited in its application to the details of construction and the arrangement of components set forth in the following description or illustrated in the following drawings. The invention is capable of other embodiments and of being practiced or of being carried out in various ways.

CD206 is a C-type lectin protein found on macrophages and other cells. In some embodiments, the present invention provides compounds, compositions and methods for the diagnosis and/or treatment of diseases mediated by CD206-high expressing cells using synthetic macromolecules. These diseases include any condition where macrophages, CD206-high expressing cells or cells that recognize certain glycolcalyx structures and their equivalents are involved or recruited, such as those where the number of macrophages or other CD206-high and/or lectin-high expressing cells is increased and/or such cells are abnormally localized (e.g., in tumors, affected joints, or anatomic regions harboring invading pathogens, etc.). Such diseases include immune diseases, autoimmune diseases, inflammatory diseases, and infectious diseases. The present invention appears, however, to target other receptors found on cells such that even non CD206-expressing cells are targeted.

The Virus Genus *Flavivirus* (Family Flaviviridae_-*Flavivirus* is a genus of viruses in the family Flaviviridae. This genus includes the West Nile virus, dengue virus, tick-borne encephalitis virus, yellow fever virus, Zika virus and several other viruses which may cause encephalitis, as well as insect-specific *Flaviviruses* (ISFs) such as cell fusing agent virus (CFAV), Palm Creek virus (PCV), and Parramatta River virus (PaRV).

Flaviviruses have a (+) sense RNA genome and replicate in the cytoplasm of the host cells. The genome mimics the cellular mRNA molecule in all aspects except for the absence of the poly-adenylated (poly-A) tail. This feature allows the virus to exploit cellular apparatuses to synthesize both structural and non-structural proteins, during replication. The cellular ribosome is crucial to the replication of the *Flavivirus*, as it translates the RNA, in a similar fashion to cellular mRNA, resulting in the synthesis of a single polyprotein. In general, the genome encodes 3 structural proteins (Capsid, prM, and Envelope) and 8 nonstructural proteins (NS1, NS2A, NS2B, NS3, NS4A, NS4B, NS5 and NS5B). The genomic RNA is modified at the 5' end of positive-strand genomic RNA with a cap-1 structure ($me^7$-GpppA-$me^2$).

Zika Virus—Zika virus (at times, referred to as ZIKV herein; a member of the virus family Flaviviridae) can cause Zika virus disease (or, at times, referred to as Zika fever) and is a member of the virus family Flaviviridae and the genus *Flavivirus*. Zika can be spread by *Aedes* mosquitoes, such as *A. aegypti* and *A. albopictus*, which are often active in the day time. Zika virus is related to dengue, yellow fever, Japanese encephalitis, and West Nile viruses, and other insect vector-spread viruses. Zika has been known to occur along the equator from Africa to Asia since the 1950s. Over recent years, the virus has spread to western continents including North America and South America.

There is no known specific treatment in the prior art, but paracetamol (acetaminophen) and rest may help with the symptoms but these treatments have failed to adequately address the issue. Prior art medications or vaccines have failed to adequately treat Zika. Zika is also especially concerning for pregnant women because the virus can spread from a pregnant woman to her fetus. This can result in microcephaly, severe brain malformations, and other birth defects. It has also recently been discovered that Zika is neurotropic even in adults. Zika infections in adults may result in temporary paralysis and in Guillain-Barre syndrome, and/or myelitis. Zika can also be sexually transmitted.

In January 2016, the United States Centers for Disease Control and Prevention (CDC) issued travel guidance on affected countries, including the use of enhanced precautions, and guidelines for pregnant women including considering postponing travel. As such, needs exist to establish a way of preventing acquisition of Zika virus.

On Feb. 1, 2016, the World Health Organization declared a Public Health Emergency of International Concern regarding neurological disorders associated with the Zika virus (ZIKV) in the Americas. Previously, ZIKV was a relatively uninvestigated mosquito-borne arbovirus in the genus *Flavivirus*, family Flaviviridae. ZIKV infections have been known in Africa and Asia since the 1940s. During the last few years, the virus caused several outbreaks across Oceania. In May 2015, a ZIKV outbreak was first reported in

| Genus | Host Details | Tissue Tropism | Entry Details | Release Details | Replication Site | Assembly Site | Transmission |
|---|---|---|---|---|---|---|---|
| *Flavivirus* | Humans; mamals; mosquitoes; ticks | Epithelium: skin; epithelium: kidney; epithelium: intestine; epithelium: testes macrophages | Clathrin-mediated endocytosis | Secretion | Cytoplasm | Cytoplasm | Zoonosis; arthropod bite |

Brazil and within months, most countries in Latin America and the Caribbean had reported local transmission of the virus. At present, neither vaccination nor specific antiviral therapies are available to prevent/treat ZIKV infections, demonstrating the international need for embodiments of the inventions described herein.

Dengue Virus: Dengue fever is a mosquito-borne tropical disease caused by the dengue virus. Symptoms can begin three to fourteen days after infection. This may include a high fever, headache, vomiting, muscle and joint pains, and a characteristic skin rash. Recovery can generally takes less than two to seven days. In a small proportion of cases, the disease develops into the life-threatening dengue hemorrhagic fever, resulting in bleeding, low levels of blood platelets and blood plasma leakage, or into dengue shock syndrome, where dangerously low blood pressure occurs.

The Dengue virus can be spread by several species of mosquito of the *Aedes* type, principally *A. aegypti*. The virus has at least five different types; infection with one type usually gives lifelong immunity to that type, but only short-term immunity to the others. Subsequent infection with a different type increases the risk of severe complications. The Dengue diagnosis can be confirmed in a number of ways, including not limited to, detecting antibodies to the virus or its RNA.

A vaccine for dengue fever has been approved in three countries, but it is not yet commercially available, which is one reason that the present disclosure demonstrates that needs exist for the present invention. Prior art treatment of acute dengue is supportive and includes giving fluid either by mouth or intravenously for mild or moderate disease. For more severe cases blood transfusion may be required. About half a million people require admission to the hospital per year as a result of contracting dengue, and as such, needs exist to prevent and/or treat dengue using compositions and methods described herein. Nonsteroidal antiinflammatory drug (NSAIDs) such as ibuprofen should not be used to prevent and/or treat dengue.

Dengue has become a global problem since the Second World War and is common in more than 110 countries. Each year between 50 and 528 million people are infected and approximately 10,000 to 20,000 die. The earliest descriptions of an outbreak date from 1779. Aspects of its viral cause and spread were understood by the early 20th century. Apart from eliminating the mosquitoes, work is ongoing for medication targeted directly at the virus, indicating that needs exist for embodiments of the invention disclosed herein and that prior art compositions and methods have failed to adequately achieve the results achieved by the present invention.

The characteristic symptoms of dengue are sudden-onset fever, headache (typically located behind the eyes), muscle and joint pains, and a rash. The alternative name for dengue, "breakbone fever", comes from the associated muscle and joint pains. The course of infection is divided into three phases: febrile, critical, and recovery. The febrile phase involves high fever, potentially over 40° C. (104° F.), and is associated with generalized pain and a headache; this usually lasts two to seven days. Nausea and vomiting may also occur. A rash occurs in 50-80% of those with symptoms in the first or second day of symptoms as flushed skin, or later in the course of illness (days 4-7), as a measles-like rash. A rash described as "islands of white in a sea of red" has also been observed. Some petechiae (small red spots that do not disappear when the skin is pressed, which are caused by broken capillaries) can appear at this point, as may some mild bleeding from the mucous membranes of the mouth and nose. The fever itself is classically biphasic or saddleback in nature, breaking and then returning for one or two days.

The rash of dengue fever in the acute stage of the infection blanches when pressed in some people, the disease proceeds to a critical phase as fever resolves. During this period, there is leakage of plasma from the blood vessels, typically lasting one to two days. This may result in fluid accumulation in the chest and abdominal cavity as well as depletion of fluid from the circulation and decreased blood supply to vital organs. There may also be organ dysfunction and severe bleeding, typically from the gastrointestinal tract. Shock (dengue shock syndrome) and hemorrhage (dengue hemorrhagic fever) occur in less than 5% of all cases of dengue, however those who have previously been infected with other serotypes of dengue virus ("secondary infection") are at an increased risk. This critical phase, while rare, occurs relatively more commonly in children and young adults.

BRIEF DESCRIPTION OF THE DRAWINGS

FIGS. 2A-2D show a series of images of MR206 expression and binding of an example of a macrophage-targeting compositions described herein.

FIG. 5 shows the infectivity reduction of Zika-containing VERO cells achieved by administration of examples of compounds described herein containing therapeutic agents.

DEFINITIONS

Figure 1A:
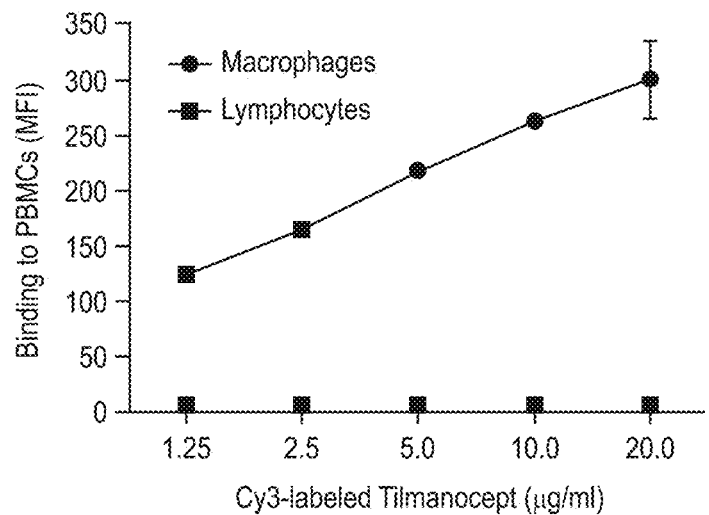
FIGS. 1A-1C show a series of images of binding of an example of a macrophage-targeting compositions described herein.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Perkin Elmer Corporation, U.S.A.).

As used in the specification, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the identification can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, intradermal administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. CD206, or other receptor), or other biological entity together in such a manner that the compound can affect the activity of the target, either directly; i.e., by interacting with the target itself, or indirectly; i.e., by interacting with another molecule, cofactor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause unacceptable adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. More than one substituent may be present. Substituents may also be themselves substituted. When substituted, the substituent group is preferably but not limited to $C_1$-$C_4$ alkyl, aryl, heteroaryl, amino, imino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. More than one substituent may be present. When substituted, the substituent group is preferably alkyl, halogen or alkoxy. Substituents may also be themselves substituted. Substituents can be placed on the alkene itself and also on the adjacent member atoms or the alkenyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. More than one substituent may be present. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl; alkenyl; alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl.

"Amino" refers to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidinyl is specifically contemplated under the term 'amino".

"Aryl" refers to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to heteroaryl, acyl, carboxyl, carbonylamino, nitro, amino, cyano, halogen, or hydroxyl.

"Carboxyl" refers to the group —C(=O)O—$C_1$-$C_4$ alkyl.

"Carbonyl" refers to the group —C(O)R wherein each R is, independently, hydrogen, alkyl, aryl, cycloalkyl; heterocycloalkyl, heteroaryl, $C_1$-$C_4$ alkyl aryl or $C_1$-$C_4$ alkyl heteroaryl.

"Carbonylamino" refers to the group —C(O)NR'R' wherein each R' is, independently, hydrogen, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. More than one substituent may be present. Substituents may also themselves be substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl; thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. More than one substituent may be present. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxy is hydroxyl.

"Leash/leashes" and "linker/linkers" may be used interchangeably herein. The term "leash" or "leashes" can often be used to refer to attachment moiety used for a targeting moiety, such as mannose. The term "linker" or "linkers" can be used to refer to the attachment moiety used for a therapeutic agent that may incorporate additional properties related to the chemistry of the linker and therapeutic agent and the delivery of the said agent. Although these terms can be used interchangeably herein, their meaning will be clear to the skilled artisan in view of the context with which it is used.

"Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. More than one substituent may be present. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Tilmanocept" refers to a non-radiolabeled precursor of the LYMPHOSEEK® diagnostic agent. Tilmanocept may be a mannosylaminodextran. It can have a dextran backbone to which a plurality of amino-terminated linkers (—O(CH$_2$)$_3$S(CH$_2$)$_2$NH$_2$) are attached to the core glucose elements. In addition, mannose moieties can be conjugated to amino groups of a number of the linkers, and the chelator diethylenetriamine pentaacetic acid (DTPA) can be conjugated to the amino group of other linkers not containing the mannose. Tilmanocept generally, has a dextran backbone, in which a plurality of the glucose residues comprise an amino-terminated linker:

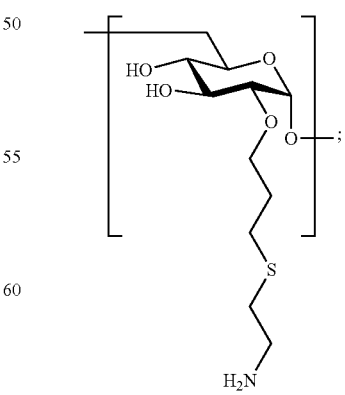

The mannose moieties are conjugated to the amino groups of the linker via an amidine linker:

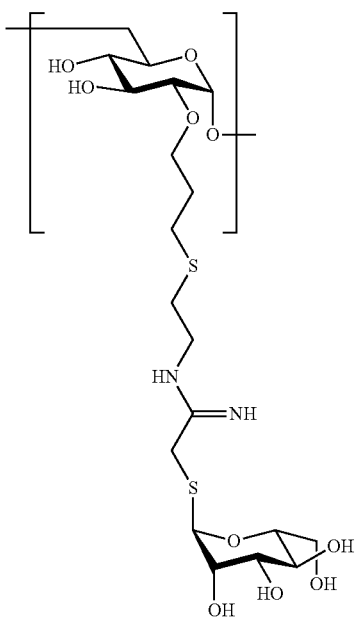

The chelator diethylenetriamine pentaacetic acid (DTPA) is conjugated to the amino groups the linker via an amide linker:

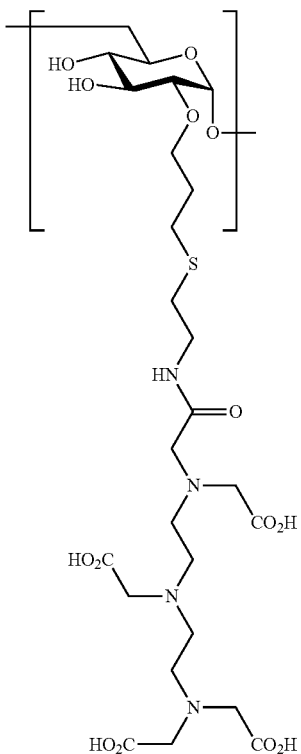

As described in the prescribing information approved for LYMPHOSEEK® in the United States, tilmanocept has the chemical name dextran 3-[(2-aminoethyl)thio]propyl 17-carboxy-10,13,16-tris(carboxymethyl)-8-oxo-4-thia-7,10,13,16-tetraazaheptadec-1-yl 3-[[2-[[1-imino-2-(D-mannopyranosylthio)ethyl]amino]ethyl]thio]propyl ether complexes, has the following molecular formula: $[C_6H_{10}O_5]n \cdot (C_{19}H_{28}N_4O_9S^{99m}Tc)_b \cdot (C_{13}H_{24}N_2O_5S_2)_c \cdot (C_5H_{11}NS)_a$, and contains 3-8 conjugated DTPA molecules; 12-20 conjugated mannose molecules; and 0-17 amine side chains remaining free. Tilmanocept has the following general structure:

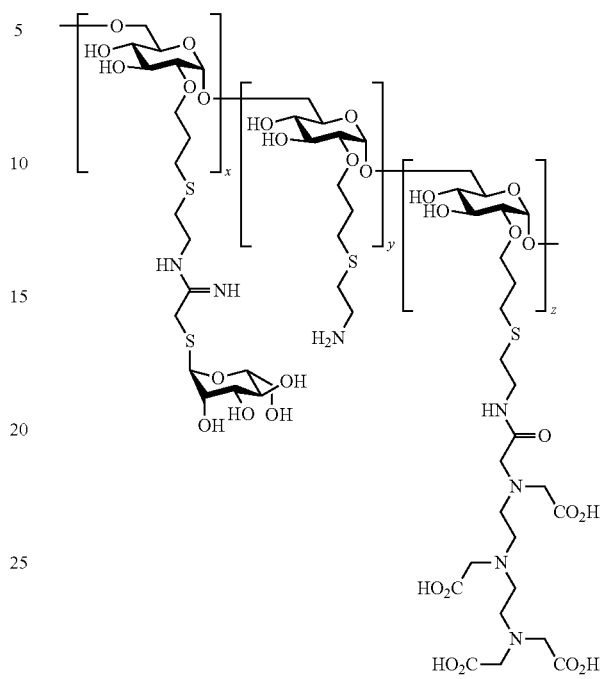

Certain of the glucose moieties may have no attached amino-terminated linker.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes may be used for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, BE, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

Embodiments of the present invention can employ a carrier construct comprising a polymeric (e.g., carbohydrate) backbone that can comprise a CD206 targeting moiety attached thereto (e.g., mannose) to deliver one or more active pharmaceutical ingredients. Examples of such constructs include mannosylamino dextrans (MAD), which can comprise a dextran backbone having conjugated to glucose residues of the backbone mannose molecules and having conjugated to other glucose residues of the backbone an active pharmaceutical ingredient. Tilmanocept is a specific example of a MAD. A tilmanocept derivative that is tilmanocept without DTPA conjugated thereto is a further example of a MAD (sometimes referred to as m-tilmanocept).

In some embodiments, the present invention provides a compound comprising a dextran-based moiety or backbone having one or more CD206 targeting moieties and one or more therapeutic agents attached thereto. The dextran-based moiety generally comprises a dextran backbone similar to that described in U.S. Pat. No. 6,409,990 (the '990 patent), which is incorporated herein by reference in its entirety. Thus, the backbone comprises a plurality of glucose moieties (i.e., residues) primarily linked by α-1,6 glycosidic bonds. Other linkages such as α-1,4 and/or α-1,3 bonds may also be present. In some embodiments, not every backbone moiety is substituted. In some embodiments, CD206 targeting moieties are attached to between about 10% and about 50% of the glucose residues of the dextran backbone, or between about 20% and about 45% of the glucose residues, or between about 25% and about 40% of the glucose residues. In some embodiments, every three glucose residues may be substituted. In some embodiments, every four glucose residues may be substituted. In some embodiments, every five glucose residues may be substituted. Some embodiments may comprise one mannose positioned on every third glucose residue. Some embodiments may comprise one mannose positioned on every fourth glucose residue. Some embodiments may comprise one mannose positioned on every fifth glucose residue. In some embodiments, the dextran-based moiety is about 50-100 kilodaltons (kDa). The dextran-based moiety may be at least about 50 kDa, at least about 60 kDa, at least about 70 kDa, at least about 80 kDa, or at least about 90 kDa. The dextran-based moiety may be less than about 100 kDa, less than about 90 kDa, less than about 80 kDa, less than about 70 kDa, or less than about 60 kDa. In some embodiments, the dextran backbone has a molecular weight (MW) of between about 1 and about 50 kDa, while in other embodiments the dextran backbone can have a MW of between about 5 and about 25 kDa. In embodiments, the dextran backbone can have a MW of between about 8 and about 15 kDa, such as about 10 kDa. While in other embodiments the dextran backbone can have a MW of between about 1 and about 5 kDa, such as about 2 kDa. Certain embodiments of compositions can comprise a backbone that is between about 1 to about 5 kDa, about 1 to about 10 kDa, about 1 to about 15 kDa, about 5 to about 12 kDa, about 5 to about 10 kDa, and ranges therebetween. In some embodiments, a composition may comprise between about 3 to about 7 mannose molecules, about 5 to about 10 mannose molecules, about 10 to about 15 mannose molecules, about 15 to about 20 mannose molecules, about 16 to about 17 mannose molecules, and ranges therebetween. In some embodiments, a backbone may be about 1 to about 3 kDa and may further comprise about 3 to about 7 mannose molecules. In some embodiments, a backbone may be about 10 kDa and may further comprise about 15 to about to about 20, or about 16 to about 17 mannose molecules. An embodiment may comprise a backbone that is about 10 kDa and further comprise about 2 therapeutic agent mole-cules, wherein the therapeutic agent molecules can comprise doxorubicin, and further comprise about 16 to about 17 mannose molecules. Such a configuration has unexpectedly superior and improved solubility, improved clarity, improved injectability and distribution, and can reduce the amount of active drug required to achieve a therapeutic result. Some embodiments may comprise therapeutic agents wherein the compositions comprises between about 1 and about 5 therapeutic agent molecules.

Some embodiments may comprise a backbone that is not a dextran backbone. Some embodiments may have a monosaccharide-based backbone that does not comprise dextran. The backbone of a carbohydrate-based carrier molecules described herein can comprise a glycan other than dextran, wherein the glycan comprises a plurality of monosaccharide residues (i.e., sugar residues or modified sugar residues). In certain embodiments, the glycan backbone has sufficient monosaccharide residues, as well as optional groups such as one or more amino acids, polypeptides and/or lipids, to provide a MW of about 1 to about 50 kDa. As would be appreciated by the skilled artisan when considering the disclosure contained herein, when referring to a "dextran" backbone, other monosaccharide residues may be considered to be substituted in compounds described herein. Additional descriptions of carbohydrate-backbone-based carrier molecules used for targeting CD206 are described in PCT application No. US/2017/055211, which is herein incorporated by reference in its entirety.

Certain embodiments of compositions can comprise a backbone that is between about 1 to about 5 kDa, about 1 to about 10 kDa, about 1 to about 15 kDa, about 5 to about 12 kDa, about 5 to about 10 kDa, and ranges there between. In some embodiments, a composition may comprise between about 2 to about 7 mannose molecules, about 5 to about 10 mannose molecules, about 10 to about 15 mannose molecules, about 15 to about 28 mannose molecules, about 16 to about 17 mannose molecules, and ranges there between. In some embodiments, a backbone may be about 1 to about 3 kDa and may further comprise about 3 to about 7 mannose molecules. In some embodiments, a backbone may be about 10 kDa and may further comprise about 15 to about to about 20, or about 16 to about 17 mannose molecules. In some embodiments, a therapeutic molecule can comprise about 1 to about 5 molecules (e.g., therapeutic agents), about 3 to 10 molecules, about 7 to about 20 molecules, and ranges therebetween. An embodiment may comprise a backbone that is about 10 kDa and further comprise about 2 therapeutic agent molecules, wherein the therapeutic agent molecules can comprise doxorubicin, and further comprise about 16 to about 17 mannose molecules. Such a configuration has unexpectedly superior and improved solubility, improved clarity, improved injectability and biodistribution, and can reduce the amount of active drug required to achieve a therapeutic result at a fraction of the free therapeutic agent.

Carrier molecules having smaller MW dextran backbones may be appropriate for instances where the molecule is desired to cross the blood-brain barrier, or when reduced residence time is desired (i.e., the duration of binding to CD206 is reduced). Carrier molecules having larger MW dextran backbones may be appropriate for instances where increased residence time is desired (i.e., the duration of circulation and exposure to CD206 is increased). In certain embodiments, carrier molecules having smaller MW dextran backbones (e.g., about 1 to about 5 kDa) may be employed when more efficient receptor substrates are attached to the dextran backbone (e.g., branched mannose moieties, as described below). More efficient receptor substrates can bind to CD206 for longer durations and/or more effectively, thus allowing for the use of smaller dextran backbones.

In some embodiments, the CD206 targeting moiety is selected from, but not limited to, mannose, fucose, galactose, n-acetylgalactosamine, and n-acetylglucosamine and combinations of these. In some embodiments, the targeting moieties are attached to between about 10% and about 50% of the glucose residues of the dextran backbone, or between about 20% and about 45% of the glucose residues, or between about 25% and about 40% of the glucose residues. (It should be noted that the MWs referenced herein, as well as the number and degree of conjugation of receptor substrates, linkers, and diagnostic/therapeutic moieties attached to the dextran backbone refer to average amounts for a given quantity of carrier molecules, since the synthesis techniques will result in some variability.)

In some embodiments, the one or more CD206 targeting moieties and one or more therapeutic agents (or drugs) and/or detection labels are attached to the dextran-based moiety through a linker. The linker may be attached at from about 50% to about 100% of the backbone moieties or about 70% to about 90%. In embodiments with multiple linkers, the linkers may be the same or different. In some embodiments, the linker is an amino-terminated linker. In some embodiments, the linkers may comprise —O(CH$_2$)$_3$S(CH$_2$)$_2$NH—. In some embodiments, the linker may be a chain of from 1 to 20 member atoms selected from carbon, oxygen, sulfur, nitrogen and phosphorus. The linker may be a straight chain or branched. The linker may also be substituted with one or more substituents including, but not limited to, halo groups, perfluoroalkyl groups, perfluoroalkoxy groups, alkyl groups, such C$_{1-4}$ alkyl, alkenyl groups, such as C$_{1-4}$ alkenyl, alkynyl groups, such as C$_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO— (C=O)— groups, heterocylic groups, cycloalkyl groups, amino groups, alkyl—and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkyl sulfonyl groups, arylsulfonyl groups, —NH—NH$_2$; =N—H; =N-alkyl; —SH; —S-alkyl; —NH—C(O)—; —NHC(=N)— and the like. Other suitable linkers would be known to one of ordinary skill in the art.

In some embodiments, the one or more therapeutic agent is attached via a biodegradable linker. In some embodiments, the biodegradable linker comprises an acid sensitive, such as a hydrazone moiety. The use of an acid sensitive linker enables the drug to be transported into the cell and allows for the release of the drug substantially inside of the cell. In certain embodiments, the linker comprises a biodegradable moiety attached to a linker.

Various other linkers known to those skilled in the art or subsequently discovered may be used in place of (or in addition to) —O(CH$_2$)$_3$S(CH$_2$)$_2$NH$_2$. These include, for example, bifunctional linker groups such as alkylene diamines (H$_2$N—(CH$_2$)$_r$—NH$_2$), where r is from 2 to 12; aminoalcohols (HO—(CH$_2$)$_r$—NH$_2$), where r is from 2 to 12; aminothiols (HS—(CH$_2$)$_r$—NH$_2$), where r is from 2 to 12; amino acids that are optionally carboxy-protected; ethylene and polyethylene glycols (H—(O—CH$_2$—CH$_2$)$_n$—OH, where n is 1-4). Suitable bifunctional diamines include ethylenediamine, 1,3-propanediamine, 1,4-butanediamine, spermidine, 2,4-diaminobutyric acid, lysine, 3,3'-diaminodipropylamine, diaminopropionic acid, N-(2-aminoethyl)-1, 3-propanediamine, 2-(4-aminophenyl)ethylamine, and similar compounds. One or more amino acids also can be employed as the bifunctional linker molecule, such as β-alanine, γ-aminobutyric acid or cysteine, or an oligopeptide, such as di- or tri-alanine.

Other bifunctional linkers include:
—NH—(CH$_2$)$_r$NH—, where r is from 2-5,
—O—(CH$_2$)$_r$—NH—, where r is from 2-5,
—NH—CH$_2$—C(O)—,
—O—CH$_2$—CH$_2$—O—CH$_2$—CH$_2$—O—,
—NH—NH—C(O)—CH$_2$—,
—NH—C(CH$_3$)$_2$C(O)—,
—S—(CH$_2$)$_r$C(O)—, where r is from 1-5,
—S—(CH$_2$)$_r$—NH—, where r is from 2-5,
—S—(CH$_2$)$_r$O—, where r is from 1-5,
—S—(CH$_2$)—CH(NH$_2$)—C(O)—,
—S—(CH$_2$)—CH(COOH)—NH—,
—O—CH$_2$—CH(OH)—CH$_2$—S—CH(CO$_2$H)—NH—,
—O—CH$_2$—CH(OH)—CH$_2$—S—CH(NH$_2$)—C(O)—,
—O—CH$_2$—CH(OH)—CH$_2$—S—CH$_2$—CH$_2$—NH—,
—S—CH$_2$—C(O)—NH—CH$_2$—CH$_2$—NH—, and
—NH—O—C(O)—CH$_2$—CH$_2$—O—P(O$_2$H)—.

The therapeutic agent can include any compound known to be useful for the treatment of a disease vectored by biting insects, such as Zika virus, dengue virus, and yellow fever. Therapeutic agents include, but are not limited to, chemotherapeutic agents, such as doxorubicin; dexamethasone; anti-infective agents, such as antibiotics (e.g. tetracycline, streptomycin, amphotericin and isoniazid), heavy metals such as antimony (e.g. pentavalent antimonials), anti-virals, anti-fungals, and anti-parasitics; immunological adjuvants; steroids; nucleotides, such as DNA, RNA, RNAi, siRNA, CpG or Poly (I:C); peptides; proteins; or metals such as silver, gallium or gadolinium, paromomycin, miltefosine, fluconazole, pentamide, Meglumine antimoniate, and combinations thereof.

In certain embodiments, the therapeutic agent is an antimicrobial drug selected from the group comprising: an antibiotic; an anti-tuberculosis antibiotic (such as isoniazid, streptamycin, or ethambutol); drugs with effect on Zika virus; drugs with effect on Dengue virus, drugs with effect on family Flaviviridae viruses; an anti-viral or anti-retroviral drug, for example an inhibitor of reverse transcription (such as zidovudin) or a protease inhibitor (such as indinavir). In certain embodiments, the therapeutic agent is an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the therapeutic agent is selected from isoniazid, doxorubicin, streptomycin, and tetracycline.

In some embodiments, the therapeutic agent comprises a high energy killing isotope which has the ability to kill macrophages and tissue in the surrounding macrophage environment. Suitable radioisotopes include: $^{210/212/213/214}$Bi, $^{131/140}$Ba, $^{11/14}$C, $^{51}$Cr, $^{67/68}$Ga, $^{153}$Gd, $^{99m}$Tc, $^{88/90/91}$Y, $^{123/124/125/131}$I, $^{111/115m}$In, $^{18}$F, $^{105}$Rh, $^{153}$Sm, $^{67}$Cu, $^{166}$Ho, $^{177}$Lu, $^{186/188}$Re, $^{32/33}$P, $^{46/47}$Sc, $^{72/75}$Se, $^{35}$S, $^{182}$Ta, $^{123m/127/129/132}$Te, $^{65}$Zn, and $^{89/95}$Zr.

In embodiments, a therapeutic agent comprises a non-radioactive species selected from, but not limited to, the group consisting of: Bi, Ba, Mg, Ni, Au, Ag, V, Co, Pt, W, Ti, Al, Si, Os, Sn, Br, Mn, Mo, Li, Sb, F, Cr, Ga, Gd, I, Rh, Cu, Fe, P, Se, S, Zn and Zr.

In some embodiments, a therapeutic agent is selected from the group consisting of cytostatic agents, alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs. By way of more specific example, the therapeutic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, isoniazid, indomethacin, gallium(III), 68gallium(III), aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calicheamicin, esperamicins, and dynemicins and combinations thereof.

In embodiments wherein the therapeutic agent is a hormone or hormone antagonist, the therapeutic agent may be selected from the group consisting of prednisone, hydroxyprogesterone, medroprogesterone, diethylstilbestrol, tamoxifen, testosterone, and aminogluthetimide and combinations thereof.

In embodiments wherein the therapeutic agent is a prodrug, the therapeutic agent may be selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that can be converted to the more active cytotoxic free drug and combinations thereof.

Examples of constructs useful in the present invention include mannosylamino dextrans (MAD) such as tilmanocept and m-tilmanocept. In some embodiments, the dextran-based moiety having at least one CD206 targeting moiety attached thereto can be a compound of Formula (I):

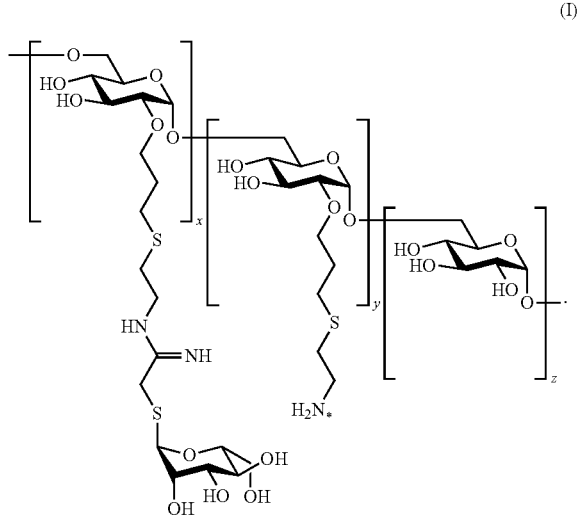

wherein the * indicates the point at which the therapeutic agent can be attached. In certain embodiments, the therapeutic agent can be attached via a linker. In certain embodiments, x can be between about 10 to about 25, about 5 to about 25, about 10 to about 20, about 15 to about 25, about 15 to about 20 and ranges therebetween. In some embodiments, y can be between about 35 and about 70, about 40 and about 70, about 50 and about 65, and ranges therebetween.

In some embodiments, z can be between about 40 to about 70, about 50 to about 65, about 50 to about 60 and ranges therebetween.

In other embodiments, the compound of the present invention can be a compound of Formula (II):

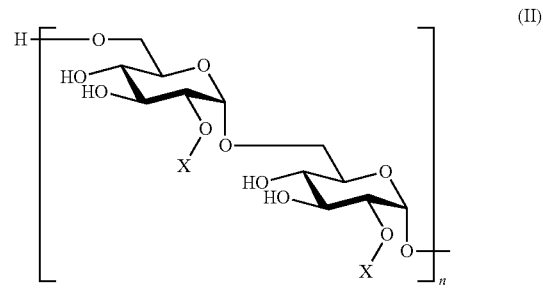

Wherein
each X is independently H, $L_1$-A, or $L_2$-R; each $L_1$ and $L_2$ are independently linkers;

each A independently comprises a therapeutic agent or a detection label or H;

each R independently comprises a CD206 targeting moiety or H; and n is an integer greater than zero.

In certain embodiments, $L_1$ is a linker as described above. In certain embodiments, $L_2$ is a linker as described above.

Synthesis

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having fewer substituents can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

The compounds of the present invention may be synthesized by any number of ways known to one of ordinary skill in the art. For example, linker 2 can be synthesized by opening succinic anhydride ring by tert-butyl carbazate. The resulting carboxylic acid is converted to the corresponding N-hydroxy succinimide (NHS) ester using EDC coupling reagent. MAD is then functionalized with linker 2 by forming an amide linkage. Then, the Boc protecting group can be removed under dilute acidic condition (typically 30-40% trifluoroacetic acid in DMSO) to obtain 4. Dilute acidic condition is required to avoid any unwanted cleavage of the glycosidic linkage present in dextran backbone. The resulting functionalized MAD can be purified by size exclusion filtration.

Scheme 1: Synthetic route A for the modification of MAD
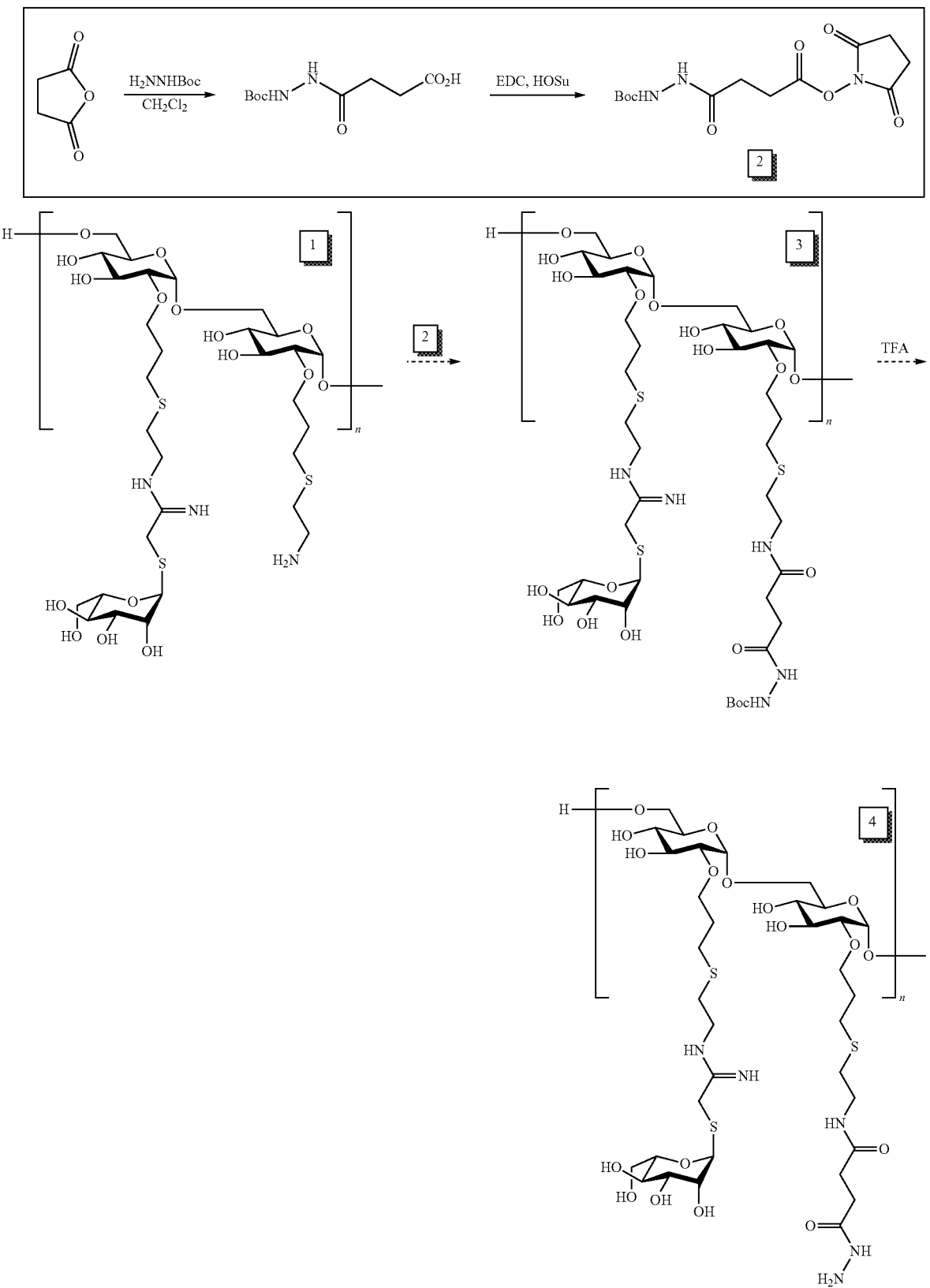

Alternatively, compounds according to the present invention may be synthesized according to Scheme 2. Free primary amine groups of MAD can be reacted with an excess of lactone under anhydrous condition. Unreacted lactone can be removed under reduced pressure to obtain modified MAD 6. The corresponding hydrazine derivative 7 can be prepared by reductive amination reaction using sodium cyanoborohydride or sodium triacetoxy borohydride as the reducing agent.

Scheme 2: Synthetic route B for the modification of MAD

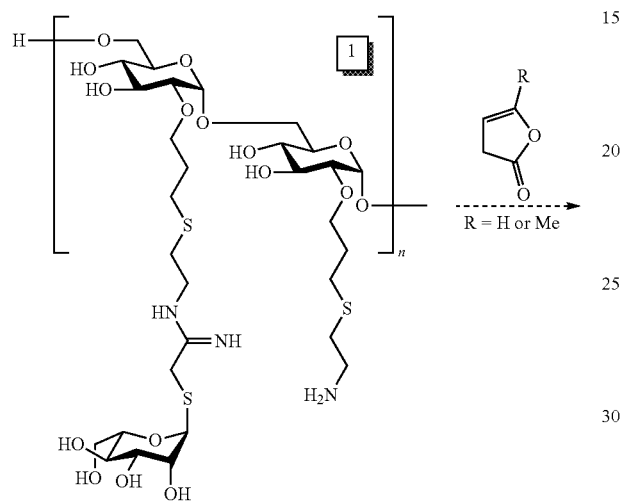

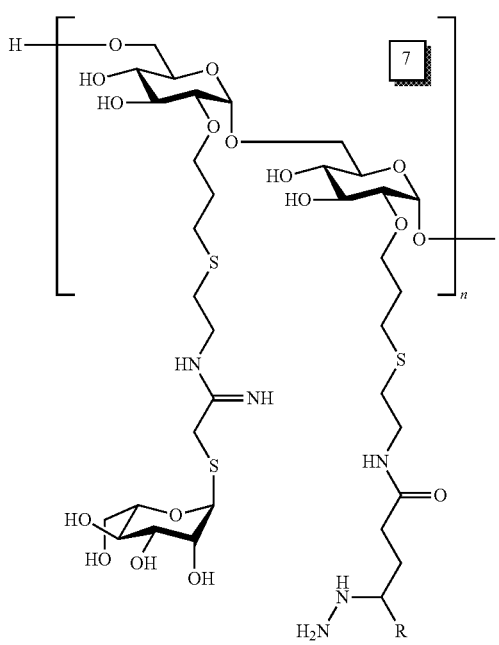

The conjugation of oxo-containing therapeutic agents to MAD derivatives 4 or 7 can be as is shown in Scheme 3. MAD derivative 4 or 7 can be conjugated to doxorubicin by formation of hydrazone linkage under anhydrous acidic condition or aqueous acidic conditions. Unconjugated therapeutic agent can be removed (e.g. by size exclusion chromatography or dialyzation) to obtain the pure conjugated MAD (indicated as m-tilmanocept in the scheme below).

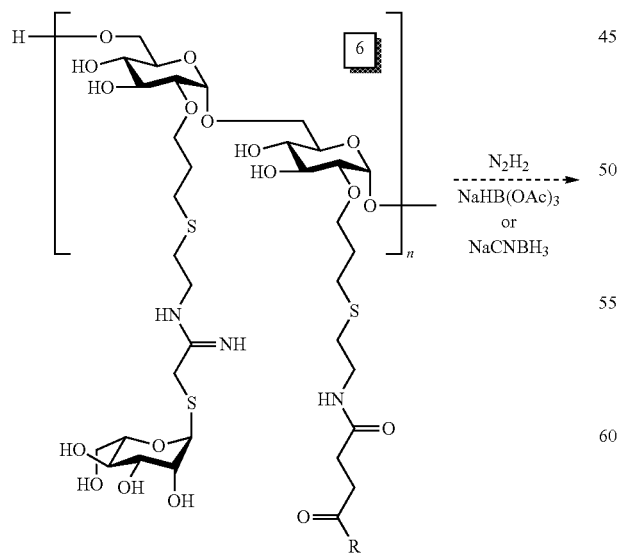

Scheme 3: Conjugation of doxorubicin to MAD derivatives

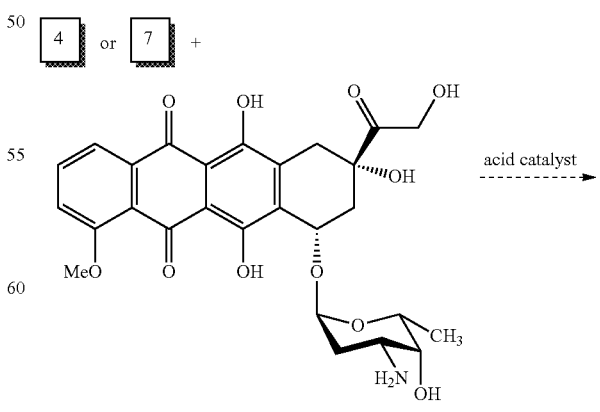

-continued

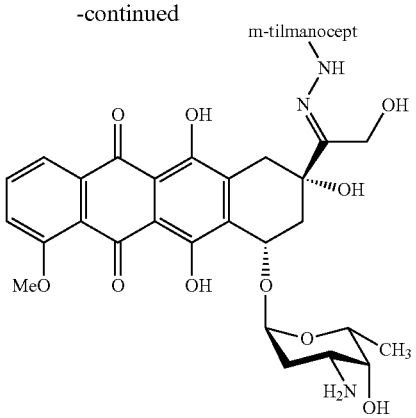

Amine-containing therapeutic agents may be conjugated to dextran-containing compounds according to Scheme 4. The basic reaction between a primary amine and the lactone are shown in Scheme 4.

Scheme 4.

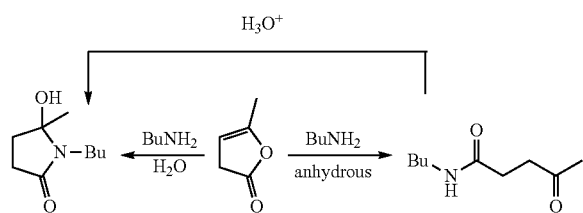

One of ordinary skill in the art would recognize other ways to synthesize the compounds of the present invention.

Pharmaceutical Compositions

Embodiments of the invention relate to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In some embodiments, the invention relates to pharmaceutical compositions comprising a pharmaceutically acceptable carrier and an effective amount of at least one disclosed compound; or a pharmaceutically acceptable salt, hydrate, solvate, or polymorph thereof.

In some embodiments, the effective amount is a therapeutically effective amount. In certain embodiments, the effective amount is a prophylactically effective amount. In some embodiments, the pharmaceutical composition comprises a compound that is a product of a disclosed method of making.

In some embodiments, the pharmaceutical composition comprises a disclosed compound. In some embodiments, the pharmaceutical composition comprises a product of a disclosed method of making.

In certain embodiments, the pharmaceutical composition is used to treat a mammal and the mammal can be a human. In some embodiments, the mammal has been diagnosed with a need for treatment of the disorder prior to the administering step. In some embodiments, the mammal has been identified to be in need of treatment of the disorder.

In certain embodiments, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, intradermal and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-di ethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as lyophilized powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood, however, that the specific dose level for any particular patient will depend upon a variety of factors and such a dosage amount would be readily ascertainable by the skilled artisan in consideration of these factors. Such factors include the age, body weight, general health, sex, and diet of the patient. Other factors include the time and route of administration, rate of excretion, drug combination, and the type and severity of the particular disease undergoing therapy.

Diagnostic Methods

Diagnostic methods are disclosed for in vivo detection of diseases or conditions using the disclosed compounds.

In certain embodiments, the disclosed compounds include a detection label in addition to the therapeutic agent. As used herein, the term "detectable label or moiety" means an atom, isotope, or chemical structure which is: (1) capable of attachment to the carrier molecule;

(2) non-toxic to humans or other mammalian subjects; and (3) provides a directly or indirectly detectable signal, particularly a signal which not only can be measured but whose intensity is related (e.g., proportional) to the amount of the detectable moiety. The signal may be detected by any suitable means, including spectroscopic, electrical, optical, magnetic, auditory, radio signal, or palpation detection means.

Detection labels include, but are not limited to, fluorescent molecules (a.k.a. fluorochromes and fluorophores), chemiluminescent reagents (e.g., luminol), bioluminescent reagents (e.g., luciferin and green fluorescent protein (GFP)), metals (e.g., gold nanoparticles), and radioactive isotopes (radioisotopes). Suitable detection labels can be selected based on the choice of imaging method. For example, the detection label can be a near infrared fluorescent dye for optical imaging, a Gadolinium chelate for MRI imaging, a radionuclide for PET or SPECT imaging, or a gold nanoparticle for CT imaging.

Detection labels can be selected from, for example, a radionuclide, a radiological contrast agent, a paramagnetic ion, a metal, a fluorescent label, a chemiluminescent label, an ultrasound contrast agent, a photoactive agent, or a combination thereof. Non-limiting examples of detectable labels include a radionuclide such as $^{110}$In, $^{111}$In, $^{177}$Lu, $^{18}$F, $^{52}$Fe, $^{62}$Cu, $^{64}$Cu $^{67}$Cu $^{67}$Ga, $^{68}$Ga, $^{86}$Y, $^{90}$Y $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P $^{11}$C, $^{13}$N, $^{15}$O, $^{186}$Re, $^{188}$Re, $^{51}$Mn, $^{2m}$Mn, $^{55}$Co, $^{72}$As, $^{75}$Br, $^{76}$Br, $^{82m}$Rb, $^{83}$Sr, $^{17m}$Sn or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas-filled liposomes.

Other suitable labels include, for example, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), near IR dyes, quantum dots, phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled molecules may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. Another modification may involve the introduction of a chelating group, for example, to chelate one of the metals or metallic cations referred to above. Suitable chelating groups, for example, include, without limitation, diethyl-enetriaminepentaacetic acid (DTPA) or ethylenediaminetetraacetic acid (EDTA). Yet another modification may comprise the introduction of a functional group that is one part of a specific binding pair, such as the biotin-(strept) avidin binding pair. Such a functional group may be used to link a disclosed compound to a protein, polypeptide or chemical compound that is bound to the other half of the binding pair, i.e., through formation of the binding pair. For example, such a conjugated molecule may be used as a reporter, for example, in a diagnostic system where a detectable signal-producing agent is conjugated to avidin or streptavidin.

Optical Imaging

The disclosed compounds can include a detectable label useful for optical imaging. A number of approaches can be used for optical imaging. The various methods depend upon fluorescence, bioluminescence, absorption or reflectance as the source of contrast. Fluorophores are compounds or moieties that absorb energy of a specific wavelength and re-emit energy at a different (but equally specific) wavelength. In certain embodiments, the detectable label is a near-infrared (NIR) fluorophore. Suitable NIRs include, but are not limited to, VivoTag-S® 680 and 750, Kodak X-SIGHT Dyes and Conjugates, DyLight 750 and 800 Fluors, Cy 5, Cy 5.5 and 7 Fluors, Alexa Fluor 680 and 750 Dyes, Alexa Fluor 688, and IRDye 680 and 800CW Fluors and combinations thereof. In certain embodiments, Quantum dots, with their photostability and bright emissions, can also be used with optical imaging.

Nuclear Medicine Imaging

The disclosed compounds can include a detectable label (e.g., a radionuclide) useful for nuclear medicine imaging. Nuclear medicine imaging involves the use and detection of radioisotopes in the body. Nuclear medicine imaging techniques include scintigraphy, single photon emission computed tomography (SPECT), and positron emission tomography (PET). In these techniques, radiation from the radioisotopes can be captured by a gamma camera to form two-dimensional images (scintigraphy) or 3-dimensional images (SPECT and PET).

Radioisotopes that can be incorporated into or attached directly to the disclosed compounds include, but are not limited to, tritium, $^{11}$C, $^{13}$N, $^{14}$C, $^{15}$O, $^{18}$Fl, $^{62}$Cu, $^{64}$Cu, $^{67}$Cu, $^{68}$Ga, $^{76}$Br, $^{82}$Rb, $^{90}$Y, $^{99m}$Tc, $^{111}$In, $^{123}$I, $^{124}$I, $^{125}$I, $^{131}$I, $^{53}$Sm, $^{201}$Tl, $^{186}$Re, $^{188}$Re, $^{17m}$Sn and $^{212}$Bi. In certain embodiments, the radioisotope is attached to a disclosed compound by halogenation. Radionuclides used in PET scanning are typically isotopes with short half-lives. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized.

Gamma radiation from radioisotopes can be detected using a gamma particle detection device. In some embodiments, the gamma particle detection device is a Gamma Finder® device (SenoRx, Irvine Calif.). In some embodiments, the gamma particle detection device is a Neoprobe® GDS gamma detection system (Dublin, Ohio).

Positron emission tomography is a nuclear medicine imaging technique which produces a three-dimensional image or picture of functional processes in the body. Some agents used for PET imaging provide information about tissue metabolism or some other specific molecular activity. Commonly used agents or potential agents that can be used as detectable agents include, but are not limited to: $^{64}$Cu diacetyl-bis(N$^4$-methylthiosemicarbazone); $^{18}$F-fluorode-oxyglucose (FDG); $^{18}$F-fluoride; 3'-deoxy-3'-[$^{18}$F]fluoro-thymidine (FLT); $^{18}$F-fluoromisonidazole; Gallium; Technetium-99m; and Thallium. Radiopaque diagnostic agents may be selected from barium compounds, gallium compounds, and/or thallium compounds. A wide variety of fluorescent labels are known in the art, including but not limited to fluorescein isothiocyanate, rhodamine, phycoerythrin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

A number of trivalent metal radionuclides have physical properties suitable for radioisotope imaging (e.g., indium-111 ($^{111}$In) gallium-67/68 ($^{67/68}$Ga) and yttrium-86 ($^{86}$Y)) or for targeted radionuclide therapy (e.g., 9° Y and lutetium-177 ($^{177}$Lu)). Diethylenetriaminepentaacetic acid (DTPA) and/or 1,4,7,10-tetraazacyclododecane-1,4,7,10-tetraacetic acid (DOTA; CAS 60239-18-1) can be used (see Choe and Lee, 2007, Current Pharmaceutical Design, 13:17-31; Li et al., 2007, J. Nuclear Medicine, "$^{64}$Cu-Labeled Tetrameric and Octameric RGD Peptides for-Small-Animal PET of Tumor avb3 Integrin Expression", 48:1162-1171; Nahrendorf et al, 2009, JACC Cardiovasc. Imaging, 2:10:1213-1222; Li et al., 2009, Mol. Cancer Ther., 8:5:1239-1249; Yim et al., 2010, J. Med. Chem., 53:3944-3953; Dijkgraaf et al., 2010, Eur. J. Nucl. Med. Mol. Imaging, published online 21 Sep. 2010; U.S. patent application Ser. No. 10/792,582; Dransfield et al., U.S. Pat. Pub. Nos. US 2010/0261875; U.S. Pat. No. 7,666,979). Of the metals mentioned, the DOTA complexes are more thermodynamically and kinetically stable than the DTPA complexes (see Sosabowski et al., Nature Protocols 1, -972-976 (2006) and Leon-Rodriguez et al., Bioconjugate chemistry, Jan. 3, 2008; 19(2):391-402).

Magnetic Resonance Imaging

The disclosed compounds can be detected via magnetic resonance imaging. MRI has the advantages of having very high spatial resolution and is very adept at morphological imaging and functional imaging. MRI generally has a sensitivity of around 10-3 mol/L to 10-5 mol/L. Improvements to increase MR sensitivity include hyperpolarization by increasing magnetic field strength, optical pumping, or dynamic nuclear polarization. There are also a variety of signal amplification schemes based on chemical exchange that increase sensitivity.

Chelating Agents

In some embodiments, a chelating agent may be attached to or incorporated into a disclosed compound, and used to chelate a therapeutic or diagnostic agent, such as a radionuclide. Exemplary chelators include but are not limited to DTPA (such as Mx-DTPA), DOTA, TETA, NETA or NOTA.

Useful chelators include, but are not limited to, DTPA, DO3A, DOTA, EDTA, TETA, EHPG, HBED, NOTA, DOTMA, TETMA, PDTA, TTHA, LICAM, HYNIC, and MECAM. HYNIC is particularly useful for chelating Tc99, another imaging agent of the invention.

Actions Based on Imaging and Identifications

The disclosed methods include the determination, identification, indication, correlation, diagnosis, prognosis, etc. (which can be referred to collectively as "identifications") of subjects, diseases, conditions, states, etc. based on imagings, measurements, detections, comparisons, analyses, assays, screenings, etc. For example, the disclosed imaging methods allow identification of patients, organs, tissues, etc. having cancer cells, metastasized cancer cells, cancer cells beyond tumor margins, etc. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical-such as paper, electronic, or other-form, for example). Thus, for example, creating a record of an identification based on the disclosed methods differs physically and tangibly from merely performing a imaging, measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different imagings, measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

Methods of Treatment

Methods of treating or preventing diseases or disorders are provided using the disclosed compounds. The disclosed compounds can be used for targeting CD206 high expressing cells and/or for targeting of macrophages for treatment of intracellular pathogens. Some embodiments as disclosed herein by target cells that do not express CD206. The disclosed compounds can be used to target tumor-associated macrophages. Some embodiments relate to methods of treating viral infections including flaviviridae viruses such as, for example but without limitation, yellow fever, dengue virus, and zika virus. Some embodiments relate to treatment of syndromes or symptoms of these, such as but not limited to, GuillanBarre syndrome.

Tilmanocept and its equivalents are discussed in PCT/US2015/041036, the entirety of which is incorporated herein by reference.

Compositions disclosed herein can be used to treat and/or diagnose Zika virus, or other viruses as disclosed herein such as yellow fever, Dengue virus, and other flaviviridae viruses. Compositions disclosed herein can be administered to a subject to prevent acquisition of Zika virus. Compositions disclosed herein can be administered to a subject exhibiting symptoms of Zika virus, to treat Zika virus and/or the symptoms of Zika virus. A subject can be exposed to compositions disclosed herein prior to infection to prevent or ameliorate infection.

In certain embodiments, agents, compounds and/or compositions comprise tilmanocept (TIL, dextran 3-[(2-aminoethyl)thio]propyl 17-carboxy-10,13,16-tris(carboxymethyl)-8-oxo-4-thia-7,10,13,16-tetraazaheptadec-1-yl-3-[[2-[[1-imino-2-(D-mannopyranosylthio)ethyl]amino]ethyl]-thio]propyl ether complexes), manocept [(MAN,17) tilmanocept sans DTPA], MAN-doxorubicin (MAN,17-DOX,5), and/or MAN-dexamethasone (MAN,17-DEX,5).

Compositions disclosed herein, such as tilmanocept and/or manocept along with their congeners, can be used as antivirals against Zika virus, Dengue, or other Flaviviridae family viruses. In certain embodiments, compositions described herein can be administered prior to conceiving a child to prevent the transmission of Zika virus, Dengue, or other Flavivrida family viruses. In some embodiments, compositions described herein can be administered to males and/or females to prevent or reduce transmission of Zika virus, Dengue, or other Flavivrida family viruses.

Macrophages make endosomes when they take up compositions described herein and the compositions described herein may not be degraded during this uptake. As discussed herein, Flaviviruses have a (+) sense RNA genome and replicate in the cytoplasm of the host cells. In certain embodiments, this replication may occur in macrophages, thus providing a way for tilmanocept compositions to deliver therapeutic agents to treat and/or prevent Zika and other flaviruses.

Without being bound by theory, human macrophages may exhibit no cytopathology from Zika viral infection. In certain embodiments, tilmanocept may be used to treat and/or prevent embryo infection wherein such an infection has occurred via transmigrating macrophages in placenta. In some embodiments, tilmanocept compositions may interact with such macrophages and deliver a therapeutic agent to treat and/or prevent embryonic Zika virus. In such embodiments, tilmanocept can treat and/or prevent birth defects caused by Zika virus, such as microcephaly.

In one experiment, Vero cells are used to test the effectiveness of tilmanocept in directing a therapeutic agent effective for treating, preventing, eliminating, and/or ameliorating Zika virus. Embodiments of tilmanocept as described herein can comprise therapeutic agents as described herein for curing, ameliorating, preventing, and/or treating Zika virus and/or the symptoms of Zika virus along with other flaviviridae viruses as discussed herein. In certain embodiments where tilmanocept is used to cure, ameliorate, prevent, and/or treat Zika virus, the tilmanocept may comprise a therapeutic agent such as doxorubicin. In certain embodiments, tilmanocept is administered to a patient to cure, ameliorate, prevent, kill, eliminate, and/or treat symptoms caused by Zika virus. To cure, ameliorate, prevent, and/or treat Zika virus, tilmanocept can be administered to a patient as described herein. In some embodiments, tilmanocept comprising a Zika virus therapeutic agent can be administered as a local intradermal injection. In certain embodiments, tilmanocept comprising a Zika virus therapeutic agent can be administered intravenously.

Tilmanocept as well as other related carrier molecules described in the '990 Patent, as well as other carrier molecules based on a dextran backbone, bind exclusively to the mannose receptor protein CD206 found on the surface of macrophages and certain other cells (e.g., Kaposi's sarcoma spindle cells) when administered to mammals or when contacted with CD206 high expressing cells ex vivo. No other receptors are believed to bind or transduce these carrier molecules, even though there are numerous other mannose receptors found in mammals. CD206 is a C-type lecithin binding protein found on the surface of macrophages and certain other types of cells. The finding that the CD206 protein, found for example on the surface of macrophages, is the sole gateway for tilmanocept binding in mammalian patients means that a MAD carrier molecule (as well as related carrier molecules) can be used as the basis for preparing a variety of therapeutically and diagnostically effective molecular species for use in the diagnosis and/or treatment of macrophage related diseases and other diseases mediated by CD206 high expressing cells.

The disclosed compounds can include therapeutic agents including, but not limited to, cytotoxic agents, anti-angiogenic agents, pro-apoptotic agents, antibiotics, hormones, hormone antagonists, chemokines, drugs, prodrugs, toxins, enzymes, or other agents. The disclosed compounds can include chemotherapeutic agents; antibiotics; immunological adjuvants; compounds useful for treating tuberculosis; steroids; nucleotides; peptides; or proteins.

In certain embodiments, the compounds include an antimicrobial drug selected from the group comprising or consisting of: an antibiotic; an anti-tuberculosis antibiotic (such as isoniazid, ethambutol); an anti-retroviral drug, for example an inhibitor of reverse transcription (such as zidovudin) or a protease inhibitor (such as indinavir); drugs with effect on leishmaniasis (such as Meglumine antimoniate), or any combination thereof. In certain embodiments, the compounds include an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the compounds include an active selected from isoniazid, doxorubicin, streptomycin, and tetracycline, or any combination thereof. The disclosed compounds can be used, for example, to treat Tuberculosis, *Staphylococcus, Streptococcus*, yeast, *Serratia. E. coli*, and *Pseudomonas aeruginosa*, Zika, and/or dengue infections.

In certain embodiments, the disclosed compounds advantageously have efficacy in the treatment of a condition, disease, or disorder caused by a micro-organism, for example, a condition, disease, or disorder including, for example, Zika and dengue.

One of ordinary skill in the art will appreciate that various kinds of molecules and compounds (e.g., therapeutic agents, detection labels, and combinations thereof) can be delivered to a cell or tissue using the disclosed compounds.

Administration

The disclosed compounds can be administered via any suitable method. The disclosed compounds can be administered parenterally into the parenchyma or into the circulation so that the disclosed compounds reach target tissues (e.g., where viral-infected cells may be located). The disclosed compounds can be administered intravenously. In still other embodiments, the disclosed compounds can be administered intraperitoneally, intramuscularly, subcutaneously, intracavity, or transdermally.

Parenteral administration of the compounds, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

EXAMPLES

Example 1. Cy3-Tilmanocept Binding to Human Macrophages

Figure 1B:
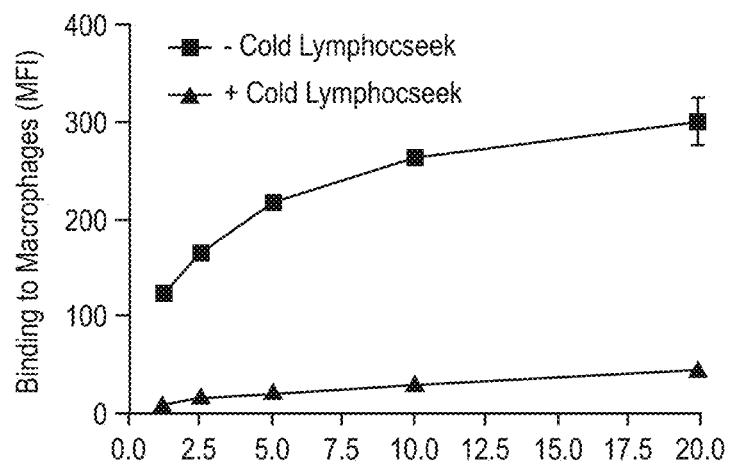

A quantity of peripheral blood mononuclear cell (PBMC)s consisting of lymphocytes or macrophages was cultured for 5 days to enable blood monocytes to differentiate into macrophages (human monocyte-derived macrophages, or "MDMs"), and then pre-treated with or without unlabeled (cold) tilmanocept. Next, the cells were incubated with varying concentrations (1.25, 2.5, 5.0, 10 and 20 µg/mL) of Cy3-labeled tilmanocept (Cy3-tilmanocept). Binding to PBMC cell populations was analyzed by flow cytometry by gating separately for macrophages and lymphocytes. The resulting data showed that Cy3-tilmanocept binds specifically to the macrophage population in a dose-dependent manner, as shown in FIG. 1A. FIG. 1A depicts fluorescence-activated cell sorting ("FACS") analysis of PBMCs, focusing on macrophages and lymphocytes. For the macrophages that were pre-treated with cold tilmanocept (100-fold excess), the binding of Cy3-tilmanocept was nearly abolished even at the highest concentrations, as shown in FIG. 1B (FACS analysis showing inhibition of tilmanocept-Cy3 binding to macrophages in presence of unlabeled tilmanocept **P<0.005).

Figure 1C:
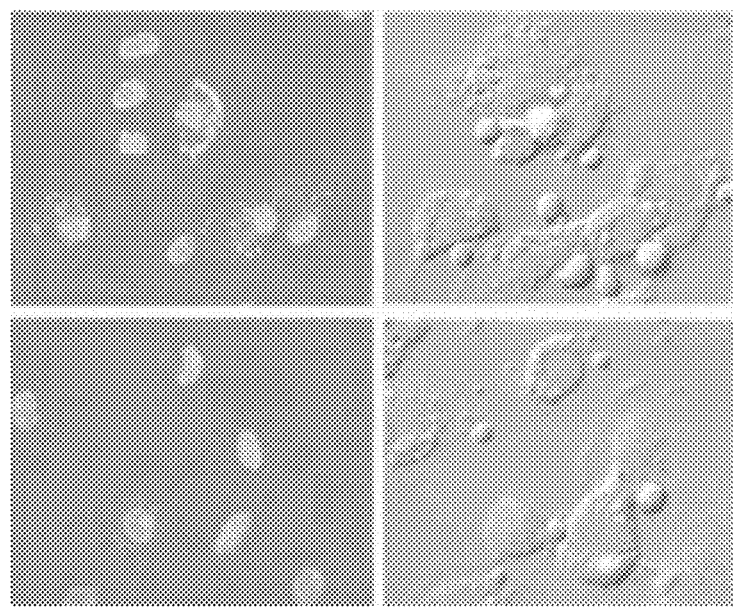

To corroborate these findings, MDMs were treated in monolayer culture in a similar way, and fluorescence confocal microscopy experiments were performed. The binding of Cy3-tilmanocept to macrophages was readily apparent and this binding was nearly abolished for macrophages that were pre-treated with cold tilmanocept, as seen in FIG. 1C. Depicted data is representative of two independent experiments, each performed in duplicate, and the results were consistent with receptor-mediated binding of Cy3-tilmanocept to macrophages. The upper and lower left images in FIG. 1C depict confocal microscopy representative images (magnification: 120×) which show binding (upper left) and inhibition of binding (lower left) of Cy3-tilmanocept to macrophages in the absence or presence of tilmanocept with no fluorophore, respectively. The gray regions indicate macrophage nuclei, and the white portions indicate Cy3-tilmanocept. The upper and lower right images in FIG. 1C are DIC images which show the individual cell structure of the adjacent fluorescent images (to the left of each DIC image). "DIC" is Differential Interference Contrast (phase contrast microscopy).

Example 2. Co-Localization of Tilmanocept with the CD206 Mannose Receptor on Human Macrophages MDM monolayers were incubated with Cy3-tilmanocept for 10 minutes, fixed with paraformaldehyde, incubated with anti-MR primary Ab, and stained with Alexa Fluor 488-conjugated secondary Ab. The monolayers were then analyzed by confocal microscopy. FIG. 2 illustrates representative confocal images (magnification: 160×) showing expression of the CD206 MR (FIG. 2A), Cy3-tilmanocept binding by the macrophage (FIG. 2B), and co-localization between the MR and Cy3-tilmanocept in both confocal and phase contrast images (FIGS. 2C and 2D). The results shown are representative of three independent experiments.

Example 3. Binding of Cy3-Tilmanocept to Macrophages Infected with Tuberculosis

Figure 3:
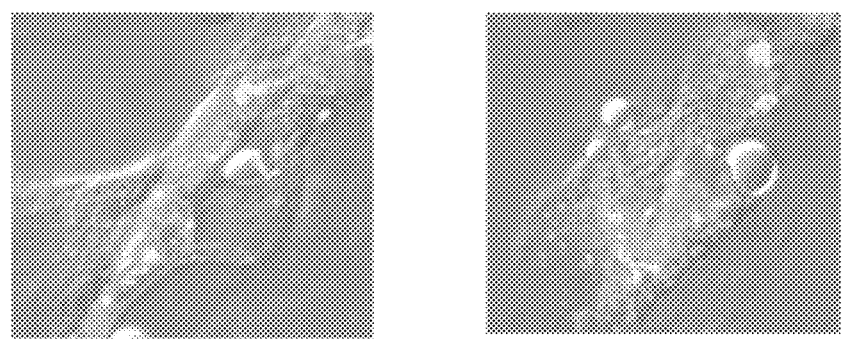
FIG. 3 shows that an example of a composition as described herein binds to, and is internalized by macrophages.
Figure 4:
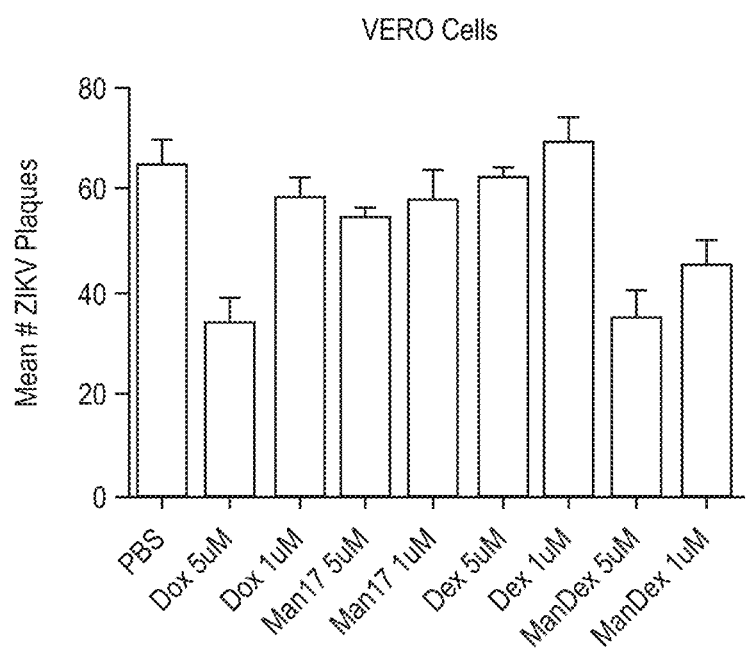
FIG. 4 shows plaque assays showing results of administration of examples of compositions described herein containing therapeutic agents.

Human monocyte-derived macrophages in monolayer culture that make up the components of the TB granulomas were infected with a GFP-expressing *M. tuberculosis* which was internalized by macrophages (GFP=green fluorescent protein). The infected cells were then exposed to Cy3-tilmanocept which had been labeled with cyanine (Cy3) dye, and analyzed by confocal microscopy. Thus, FIG. 3 demonstrates that the Cy3-tilmanocept binds to, and is internalized by the macrophages.

Example 4. Using Tilmanocept for Zika Virus-Infected VEROS Cells

African Green Monkey kidney epithelial cells (Vero; ATCC #CCL-81) and a clone of standard Vero cells (E6; ATCC #CRL-1586) are grown in minimal essential medium (MEM; Gibco, Carlsbad, CA) supplemented with 10% fetal bovine serum (FBS; Hyclone, Logan, UT), 2 mM L-glutamine, 1.5 g/l sodium bicarbonate, 100 U/ml of penicillin, 100 µg/ml of streptomycin, and incubated at 37° C. in 5% $CO_2$.

Human monocyte-derived macrophage isolation—Human peripheral blood monocyte-derived macrophages (human PCMBs, which can also be referred to as HPBM) may be purchased from appropriate commercial vendors. Alternatively, human PBMCs is isolated from heparinized blood from healthy donors (from Red Cross buffy coat preparations—upon request) on a Ficoll-Hypaque (Amersham, Pittsburgh, PA) cushion and cultured in Teflon wells in RPMI 1640+20% autologous serum for 5 days at 37° C., 5% CO2 (19), during which time monocytes differentiate into monocyte-derived macrophages (MDMs). Such cells are used in suspension or as purified MDMs in monolayer culture. Experiments are performed in duplicate or triplicate wells.

Zika or Dengue virus screens and titrations for virus quantification can be completed by plaque assay on Vero cell cultures. Duplicate wells are infected with 0.1 ml aliquots from serial 10-fold dilutions in growth media and virus is adsorbed for one hour. Following incubation, the inoculum is removed, and monolayers are overlaid with 3 ml containing a 1:1 mixture of 1.2% oxoid agar and 2× DMEM (Gibco, Carlsbad, CA) with 10% (vol/vol) FBS and 2% (vol/vol) penicillin/streptomycin. Cells are incubated at 37° C. in 5% CO2 for up to four days for plaque development. Cell monolayers then are stained with 3 ml of overlay containing a 1:1 mixture of 1.2% oxoid agar and 2× DMEM with 2% (vol/vol) FBS, 2% (vol/vol) penicillin/streptomycin, and 0.33% neutral red (Gibco). Cells are incubated overnight at 37° C. and plaques are counted.

TIL and MAN,17 congeners as well as fluorescent congeners are supplied by Macrophage Therapeutics (MT; a subsidiary of Navidea Biopharmaceuticals, Dublin, OH). The test compounds and their specifications (the $K_d$ range for the agents is $3\times10^{-11}$ to $1\times10^{-10}$ M; molecular weights, mole ratios of core molecules to active conjugated drug, e.g. dextran/mannose to doxorubicin) are supplied by MT. Agents may be solubilized in isotonic saline or PBS to produce stock solutions as may be used in the blocking, inhibition, or fate evaluations. Concentrations of the MAN, 17 or TIL or other congeners can be based on a molecular weight of 20 kDa. Anticipated starting concentrations will be in the about 10 nM to about 1 µM range.

A viral infectivity inhibition assay is performed to measure the antiviral efficacy of TIL and MAN,17 congeners in cell culture.

Vero cells or human macrophages are seeded in 24-well plates (approximately $2\times10^4$ cells per well) and incubated without the presence of a drug for 24 hours to form a confluent monolayer. Following incubation, the medium is aspirated from the wells and replaced with 200 µl of fresh designated medium containing 500 nM of the test compound (three wells per compound), which is inoculated with Zika virus at a multiplicity of infection (MOI) that can be determined prior to the time the test compounds are added. As a negative control, vehicle is added to virus-infected and mock-infected cells at a final concentration of 0.5% (v/v). Additionally, MAN,17 is used as a negative control. Culture medium is monitored for 5 days postinfection (p.i.) to yield a 70-90% cytopathic effect (CPE) in virus control wells using a microscope equipped with a camera. To quantify the CPE, culture media is collected at the end of the experiment (i.e., day 5 p.i.) and cell death is determined using the CytoTox 96 Non-Radioactive Cytotoxicity Assay (Promega; Madison, WI) according to the Manufacturer's instructions.

Viral titers are determined by plaque assay and expressed as PFU/m. For dose-response studies, Vero cell monolayers can be cultured with 200 μl of medium containing the test compounds over the concentration range, and Zika virus at an MOI of 0.01. Drug addition and virus infection can be done at the same time with medium change time to be determined. The medium is collected from the wells at 2 and 3 days p.i., the viral titers can be determined by plaque assay and can be used to construct Zika Virus dose-response curves. The dose-response curves on day 2 p.i. can be used to estimate the 50% effective concentration (EC50). To measure the compound-induced inhibition of viral surface antigen expression, a cell-based *Flavivirus* immunostaining assay is performed as described herein. For determination of nucleoside analogue cytotoxicity, a colorimetric assay utilizing Dojindo's highly water-soluble tetrazolium salt (Cell Counting Kit-8, Dojindo Molecular Technologies; Rockville, MD) and CytoTox 96 Non-Radioactive Cytotoxicity Assay (Promega; Madison, WI) can be utilized. The concentration of compound that reduced cell viability by 50% is considered as the 50% cytotoxic concentration (CC50).

Tilmanocept fate evaluation can be based on the use of Til-Alexa 488 or Til-Cy5 fluorescent congeners. The use of these agents in tracking the fate of tilmanocept can provide binding, internalization and blocking potential interactions with chosen cell models.

Zika virus generally causes a benign disease, but in some patients the infection can manifest as myelitis or meningoencephalitis, or can trigger Guillain-Barre syndrome, a severe neurological disorder characterized by progressive muscle weakness that can result in respiratory failure. No effective therapy for Zika virus infection is available at present.

Dengue virus—Infection with any of the dengue serotypes may be asymptomatic in the majority of cases or may result in a wide spectrum of clinical symptoms, ranging from a mild flu-like syndrome (known as dengue fever [DF]) to the most severe forms of the disease, which are characterized by coagulopathy, increased vascular fragility, and permeability (dengue hemorrhagic fever [DHF]). The latter may progress to hypovolemic shock (dengue shock syndrome [DSS]). Like Zika virus, no effective therapy for Dengue virus infection is available at present.

Vero cells infected with Zika virus showed an unexpected 99.9% reduction after administering tilmanocept comprising a therapeutic agent. Doxorubicin is used as a therapeutic agent. In an example, prior to administration there was $3\times10^6$ Zika virions/mL and after administration of tilmanocept comprising doxorubicin to a subject, this unexpectedly went down to $2\times10^3$ Zika virions/mL. Plaque assays are prepared showing results, an example of which is shown as FIG. 4. FIG. 4 shows the results of administration of (1) a control containing phosphate-buffered saline (PBS); (2) 5 μM doxorubicin (Dox 5 μM); 1 μM doxorubicin (Dox 1 μM); 5 μM tilmanocept containing 17 mannoses (Man17 5 μM); 1 μM tilmanocept containing 17 mannoses (Man17 1 μM); 5 μM dexamethasone (Dex 5 μM); 1 μM dexamethasone (Dex 1 μM); 5 μM tilmanocept containing 17 mannoses and dexamethasone (ManDex 5 μM); and 1 μM tilmanocept containing 17 mannoses and dexamethasone (ManDex 1 μM). FIG. 4 shows the superior and unexpected results of use of tilmanocept in conjunction with a therapeutic agent (e.g., dexamethasone) of reducing Zika infection in VERO cells. ManDex 5 μM and ManDex 1 μM showed significantly improved results over administration of dexamethasone alone. Additional results are also shown in FIG. 5. FIG. 5 shows the percent of infectivity of VERO cells after administration of the solutions discussed with respect to FIG. 4. Similarly unexpectedly improved results were achieved via administration of ManDex 5 μM and ManDex 1 μM, which showed a dramatically improved reduction in Zika infectivity. Tilmanocept administered without a therapeutic agent had no effect. Free drug administration had very little effect. This demonstrates the unexpected results that tilmanocept and derivatives thereof, in combination with a therapeutic agent, can be effective in substantially reducing the amount of virus present in a subject along with adequately targeting cells infected with Zika virus.

Vero cells have a receptor that has lower affinity than that of macrophages (i.e., no CD206). As mentioned above, administration of tilmanocept showed a 99.9% reduction of Zika virus. This demonstrates the unexpected and superior results of tilmanocept to show that it has affinity for multiple receptors. Tilmanocept can have affinity to human dendritic cells, human skin fibroblasts, human and placental macrophages, and can deliver therapeutic agents to these cells if they are infected with Zika virus.

Figure 6:
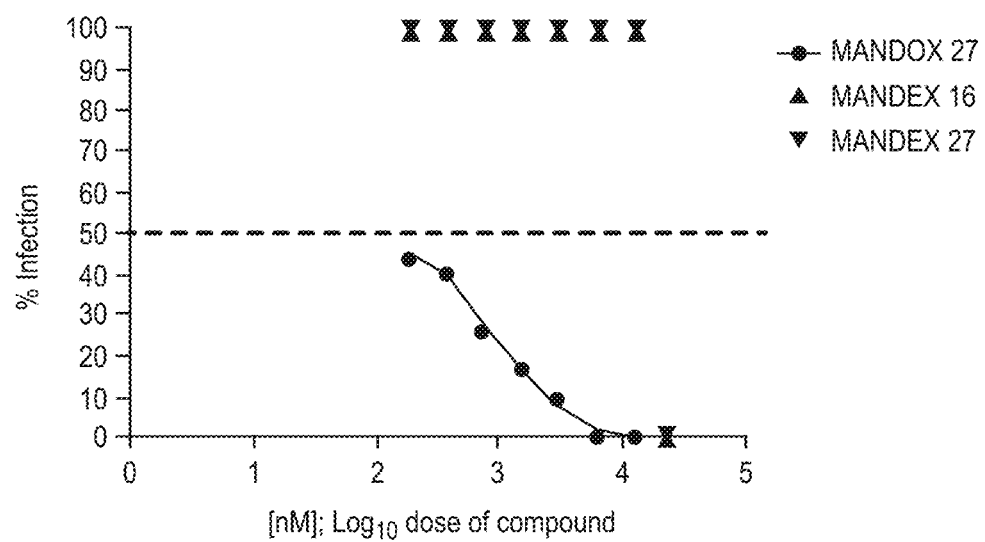
FIG. 6 shows the results of administration of examples of compounds described herein to activated Zika-containing human macrophages.

Example 5. Administration of Tilmanocept Virus to Human Cells Infected with Zika Virus Human activated macrophages were infected with the Zika virus under standard conditions using methods known to those of skill in the art. Those macrophages were cultured and then tilmanocept constructs containing therapeutic agents were administered and then compared to a control group that received no tilmanocept. Three tilmanocept constructs were administered: (1) a tilmanocept containing 16 mannoses and dexamethasone (MANDEX16); (2) a tilmanocept containing 27 mannoses and dexamethasone (MANDEX27); and (3) a tilmanocept containing 27 mannoses and doxorubicin (MANDOX27). Each of these was administered to the macrophage cultures at increasing doses as is shown in FIG. 6. FIG. 6 shows the superior and unexpected results of the reduction of infection amounts achieved after administration of MANDOX27 as follows:

TABLE 1

| Approximate Dosage Amount | MANDEX16 % Infection Remaining after administration | MANDEX27 % Infection Remaining after administration | MANDOX27 % Infection Remaining after administration |
|---|---|---|---|
| 200 nM | 0 | 0 | ~55 |
| 400 nM | 0 | 0 | ~40 |
| 800 nM | 0 | 0 | ~78 |
| 2 μM | 0 | 0 | ~82 |
| 4 μM | 0 | 0 | ~90 |
| 8 μM | 100 | 100 | 100 |

Table 1 shows that the administration of MANDOX 27 resulted in a reduced infection amount wherein that reduction increased with increases in dosage rates until 100% of the infection was reduced. The infection reduction was measured using methods known to those of skill in the art. Without being bound by theory, it is believed that the sudden reduction from zero to 100% shown by the administration of 8 μM MANDEX16 and MANDEX27 was a result in total cellular death as a result of cytotoxicity.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method of treating a disease caused by infection by a flaviviridae family virus comprising administering to a subject in need thereof an effective amount of a compound of Formula (II):

wherein each X is independently H, L1-A, or L2-R; each L1 and L2 are independently linkers;

each A independently comprises a therapeutic agent or a detection label or H;

each R independently comprises a CD206 targeting moiety or H; and n is an integer greater than zero;

wherein at least one R is a CD206 targeting moiety and at least one A is a chemotherapeutic agent.

2. The method of claim 1, wherein a linker is used to attach the one or more CD206 targeting moieties and/or one or more chemotherapeutic agent.

3. The method of claim 1, wherein at least one L1 comprises a degradable linker.

4. The method of claim 1, wherein at least one L1 comprises a hydrolysable linker.

5. The method of claim 1, wherein at least one L1 comprises an acid-sensitive linker.

6. The method of claim 1, wherein at least one L1 is a C2-12 hydrocarbon chain optionally interrupted by up to three heteroatoms selected from the group consisting of O, S and N.

7. The method of claim 1, wherein at least one L1 comprises —$(CH_2)pS(CH_2)qNH$-, wherein p and q are integers from 0 to 5.

8. The method of claim 1, wherein at least one L2 is a $C_2$-12 hydrocarbon chain optionally interrupted by up to three heteroatoms selected from the group consisting of O, S and N.

9. The method of claim 1, wherein at least one L2 comprises —$(CH_2)pS(CH_2)qNH$-, wherein p and q independently are integers from 0 to 5.

10. The method of claim 1, wherein treatment is effective through binding of the compound to the CD206 expressing cells of the subject and not through binding to the virus.

11. The method of claim 1, wherein administration of the compound treats the disease and decreases disease causing virus through binding of the subject's CD206 expressing cells.

12. A method of targeting a flaviviridae family virus by targeting macrophages comprising administering to a subject in need thereof an effective amount of a compound of Formula (II):

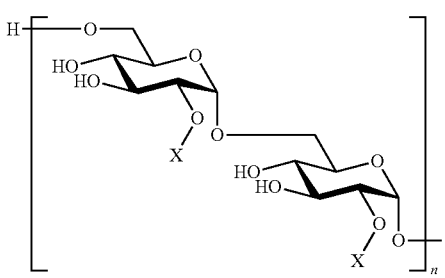

(II)

wherein each X is independently H, L1-A, or L2-R;
each L1 and L2 are independently linkers;
each A independently comprises a therapeutic agent or a detection label or H;
each R independently comprises a CD206 targeting moiety or H; and
n is an integer greater than zero;
wherein at least one R is a CD206 targeting moiety and at least one A is a chemotherapeutic agent to treat the disease and decrease the amount of disease-causing virus.

13. The method of claim 12, wherein administration of the compound treats the disease and decreases disease causing virus through binding of the subject's CD206 expressing cells.

14. The method of claim 12, wherein the chemotherapeutic agent is selected from the group consisting of a cytostatic agent, an alkylating agent, an antimetabolite agent, an antiproliferative agent, a tubulin binding agent, an anthracycline drug that is not doxorubicin, a *vinca* drug, a podophyllotoxin drug, a toxic enzyme drug, a radiosensitizing drug, and a combination thereof.

15. A method of treating a disease caused by infection by a flaviviridae family virus comprising administering to a subject in need thereof an effective amount of compound comprising a dextran backbone having one or more CD206 targeting moieties and one or more chemotherapeutic agents attached thereto.

16. The method of claim 15, wherein treatment is effective through binding of the compound to the CD206 expressing cells of the subject and not through binding to the virus.

17. The method of claim 15, wherein administration of the compound treats the disease and decreases disease causing virus through binding of the subject's CD206 expressing cells.

18. The method of claim 15, wherein a linker is used to attach the one or more CD206 targeting moieties and/or one or more chemotherapeutic agent.

19. The method of claim 18, wherein the linker comprises a degradable linker.

20. The method of claim 18, wherein the linker comprises a hydrolysable linker.

* * * * *